(12) United States Patent
Bryan

(10) Patent No.: US 6,443,987 B1
(45) Date of Patent: Sep. 3, 2002

(54) SPINAL VERTEBRAL IMPLANT

(76) Inventor: Donald W. Bryan, 6151 S. Woodland, Ogden, UT (US) 84403

(*) Notice: Subject to any disclaimer, the term of this patent is extended or adjusted under 35 U.S.C. 154(b) by 0 days.

(21) Appl. No.: 09/662,434

(22) Filed: Sep. 15, 2000

(51) Int. Cl.[7] .................................................. A61F 2/44
(52) U.S. Cl. .................................................. 623/17.11
(58) Field of Search ........................... 623/17.11–17.16

(56) References Cited

U.S. PATENT DOCUMENTS

| | | | |
|---|---|---|---|
| 3,848,601 A | 11/1974 | Ma et al. | 128/305 |
| 4,742,256 A | 5/1988 | Brantigan | 623/17 |
| 4,834,757 A | 5/1989 | Brantigan | 623/17 |
| 4,877,020 A | 10/1989 | Vich | 128/92 V |
| 5,425,772 A | 6/1995 | Brantigan | 623/17 |
| 5,522,904 A | 6/1996 | Moran et al. | 623/22 |
| 5,716,415 A | 2/1998 | Steffee | 623/17 |
| 5,766,252 A | 6/1998 | Henry et al. | 623/17 |
| 5,814,084 A | 9/1998 | Grivas et al. | 623/16 |

(List continued on next page.)

OTHER PUBLICATIONS

University of Florida Tissue Bank, Inc.: Cover Page, Available, on information and belief, more than one year prior to Sep. 15, 2000.
University of Florida Tissue Bank, Inc.: Case Study Review, *Threaded Cortical Bone Dowel: 12 Month Radiographic Analysis*, Nov. 1997.
University of Florida Tissue Bank, Inc.: Case Study Review, *Threaded Cortical Bone Dowel: A Four to Eight Month Radiographic Analysis—CT Scans*, Aug., 1997.
University of Florida Tissue Bank, Inc.: Case Study Review, *MDII Threaded Cortical Bone Dowel: A Six to Nineteen Month Radiographic Analysis—CT Scans*, Apr. 1998.
University of Florida Tissue Bank, Inc.: Case Study Review, *MDIII Threaded Cortical Bone Dowel: A Three to Six Month Radiographic Analysis—CT Scans Utilizing the Posterior Approach*, Apr. 1998.
University of Florida Tissue Bank, Inc.: Case Study Review, *Threaded Cortical Bone Dowel: The Use of a Threaded Cortical Bone Dowel incorporating a Posterior Approach*, Mar. 1997.
University of Florida Tissue Bank, Inc.: Technical Monograph, *Threaded Cortical Dowel "Construct Stiffness Testing,"* Copyright 1997.

(List continued on next page.)

*Primary Examiner*—David H. Willse
*Assistant Examiner*—Suzette J. Jackson
(74) *Attorney, Agent, or Firm*—Workman, Nydegger and Seeley

(57) ABSTRACT

A spinal vertebral implant includes a substantially rectangular shaped base section made from a solid piece of bone. A nose section extends integrally from the substantially rectangularly shaped base section and preferably has a generally tapering shape to foster entry between adjacent vertebrae. The nose section tapers distally and inwardly from the base section to form a generally pointed or rounded distal tip portion and comprises a solid piece of bone. Serrated sides assist the implant in gripping adjacent upper and lower vertebrae and in being maintained therebetween. The serrated sides are angled in a manner that encourages the implant to be placed between the vertebrae and locked therebetween upon such placement. First and second implants may be placed into respective left and right sides of an intervertebral space. A method for placing one or more implants between the adjacent vertebrae comprises forming a slot configured to receive an implant and inserting the implant into the slot. Each slot is preferably formed from an upper slot portion and a lower slot portion in the posterior portion of adjacent upper and lower vertebrae, respectively. Instruments for performing the method include osteotomes, impactors, and spacers.

20 Claims, 12 Drawing Sheets

U.S. PATENT DOCUMENTS

| | | | |
|---|---|---|---|
| 5,865,847 A | 2/1999 | Kohrs et al. ................... | 623/17 |
| 5,895,426 A | 4/1999 | Scarborough et al. ......... | 623/17 |
| 5,899,939 A | 5/1999 | Boyce et al. ................... | 623/16 |
| 5,947,965 A | 9/1999 | Bryan .......................... | 606/61 |
| 6,004,326 A | 12/1999 | Castro et al. ................... | 606/99 |
| 6,007,576 A | 12/1999 | McClellan ..................... | 623/1 |
| 6,025,538 A | 2/2000 | Yaccarino, III .............. | 623/16 |
| 6,033,438 A | 3/2000 | Bianchi et al. ................ | 623/17 |
| 6,037,519 A | 3/2000 | McKay ........................ | 623/16 |
| 6,042,582 A | 3/2000 | Ray ............................. | 606/61 |
| 6,045,580 A | 4/2000 | Scarborough et al. ......... | 623/17 |
| 6,074,390 A | 6/2000 | Zucherman et al. .......... | 606/61 |
| 6,090,112 A | 7/2000 | Zucherman et al. .......... | 606/61 |
| 6,093,207 A | 7/2000 | Pisharodi ............... | 623/17.016 |
| 6,096,038 A | 8/2000 | Michelson ................... | 606/61 |
| 6,096,081 A | 8/2000 | Grivas et al. ............ | 623/17.11 |
| 6,143,033 A * | 11/2000 | Paul et al. ................ | 623/17.11 |
| 6,149,652 A | 11/2000 | Zucherman et al. .......... | 606/61 |
| 6,174,311 B1 | 1/2001 | Branch et al. ................ | 606/61 |
| 6,200,322 B1 | 3/2001 | Branch et al. ................ | 606/96 |
| 6,206,923 B1 * | 3/2001 | Boyd et al. .............. | 623/17.11 |
| 6,224,595 B1 | 5/2001 | Michelson ................... | 606/61 |
| 6,224,607 B1 | 5/2001 | Michelson ................... | 606/96 |
| 6,238,397 B1 | 5/2001 | Zucherman et al. .......... | 606/61 |
| 6,241,729 B1 | 6/2001 | Estes et al. .................... | 606/61 |
| 6,267,763 B1 | 7/2001 | Castro ......................... | 606/61 |
| 6,270,528 B1 * | 8/2001 | McKay .................... | 623/17.11 |
| 6,277,149 B1 * | 8/2001 | Boyle et al. ............. | 623/17.11 |
| 6,280,444 B1 | 8/2001 | Zucherman et al. .......... | 606/61 |
| 6,283,966 B1 | 9/2001 | Houfburg .................... | 606/61 |
| 6,332,896 B1 | 12/2001 | Hubbard et al. ......... | 623/23.24 |

OTHER PUBLICATIONS

University of Florida Tissue Bank, Inc.: Technical Monograph, *Threaded Cortical Dowel: "Mechanical Characteristics and Evaluation,"* On information and belief, available at least as early as Aug. 1998.

University of Florida Tissue Bank, Inc.: Technical Monograph, *Threaded Cortical Dowel: "Effect of Gamma Irradiation on Allograft Bone,"* On Information and belief, available at least as early as Aug. 1998.

University of Florida Tissue Bank, Inc.: Technical Monograph, *Threaded Coritcal Dowel: "Processing and Screening Methods,"* Copyright 1996.

University of Florida Tissue Bank, Inc.: Technical Monograph, *MD–III Threaded Cortical Dowel: "Mechanical Characteristics and Evaluation,"* On information and belief, available at least as early as Aug. 1998.

University of Florida Tissue Bank, Inc.: Technical Monograph, *MD–II Threaded Cortical Dowel Maximum Pushout Load,* On information and belief, available at least as early as Aug. 1998.

*Guidelines for Reimbursement: Threaded Cortical Bone Dowel,* Mar. 1998.

Northwest Tissue Center, *Bryan Bone Block,* Mar. 2000.

Ducker, Thomas, M.D., Raymond Haroun, M.D., Seth Zeidman, M.D., and Michael Janssen, D.O., *A Safer Posteior Lumbar Interbody Fusion,* 1999.

Flyer: University of Florida Tissue Bank, Inc., *MD–I and MD–II Custom Machined Cortical Dowels,* On information and belief, available at least as early as Aug. 1998.

University of Florida Tissue Bank, Inc., *MD–III Threaded Cortical Dowel: Design Rationale and Surgical Technique,* On information and belief, available at least as early as Aug. 1998.

Sofamor Danek USA: The Spine Specialist, *Laparoscopic Bone Dowel Instruments,* copyright 1995.

Sofamor Danek USA: The Spine Specialist, *Surgical Technique Using Bone Dowel Instrumentation: For Interior Approach,* copyright 1996.

Program Guide: *Threaded Constructs for Interbody Spine Surgery,* developed by Burkus, J. Kenneth, M.D., John D. Dorchak, M.D., Regis W. Haid, Jr., M.D., Stephen E. Heim, M.D., Scott h. Kitchel, M.D., Chester E. Sutterlin, M.D., and Lawrence M. Boyd, M.D, Aug. 15, 1998.

Yuan, Hansen A., M.D., Stephen D. Kuslich, M.D., John A. Dowdle Jr., M.D., Cynthia L. Ulstrom, R.N., and Steven L. Griffith, Ph.D., *Prospective Multi–Center Clinical Trial of The BAK™ Interbody Fusion System,* 1998.

*BAK™ Interbody Fusion System,* SPINETECH Inc., 1998 (2 pages).

Bryan, Donald W., M.D., *Posterior Lumbar Fusion Using Tibial Cortical Allograft and Pedicle Screw Fixation: Scientific Exhibit AAOS,* presented at the Annual Meeting of the American Academy of Orthopedic Surgeons at Anaheim, California, Mar. 7–12, 1991.

Bryan, Donald W., M.D., Abstract, presented at the Annual Meeting of the North American Spine Society (NASS) at Minneapolis, Minnesota, Oct. 19–22. 1994.

Bryan, Donald W., M.D., *A Long Term Radiographic Analysis: Cortical Bone PLIF, Iliac Crest PLF with Pedicle Screw Instrumentation,* presented at the North American Spine Society (NASS)–Japanese Combined Meeting, Jul. 2000.

Video Cassette: "Allograft Cortical Bone PLIF Autograft ILIAC Crest PLF Contour Spinal Fixation Sistem," Jun. 2000.

Bryan, Donald W., M.D., Complete Paper Number 264: A long Term Radiographic Analysis: Corticle Bone PLIF, ILIAC Crest PLF With Pedicle Screw Instrumentation, presented at the 2001 Annual Meeting of the American Academy of Orthopedic Surgeons at San Francisco, California, Mar. 2, 2001.

Society of Military Orthopaedic Surgeons 34th Annual Meeting, Arthrodesis of the Lumbar Spine Using Posterior Lumbar Interbody Cortical Tibial Allografts, Posterior–Lateral ILIAC Crest Autografts, and Pedicle Screw Internal Fixation, Nov. 29—Dec. 4, 1992.

Bryan, Donald William, M.D., Abstract, Paper #110: The Treatment of Patients With Failed Lumbar Disc Surgery by Wide Decompression and Fussion Using Posterior Interbody Cortical Allografts, Posterior–Lateral ILIAC Crest Augografts and Pedicle Screw Internal Fixation, 2nd International Meeting On Advanced Spine Techniques, Apr. 26–29, 1995.

Bryan, Donald W., M.D., Abstract: *Wide Decompression and Posterior 360 Degree Spinal Fusion for Failed Lumbar Disc Surgery,* North American Spine Society, Minneapolis, MN, Oct. 19–22, 1994.

\* cited by examiner

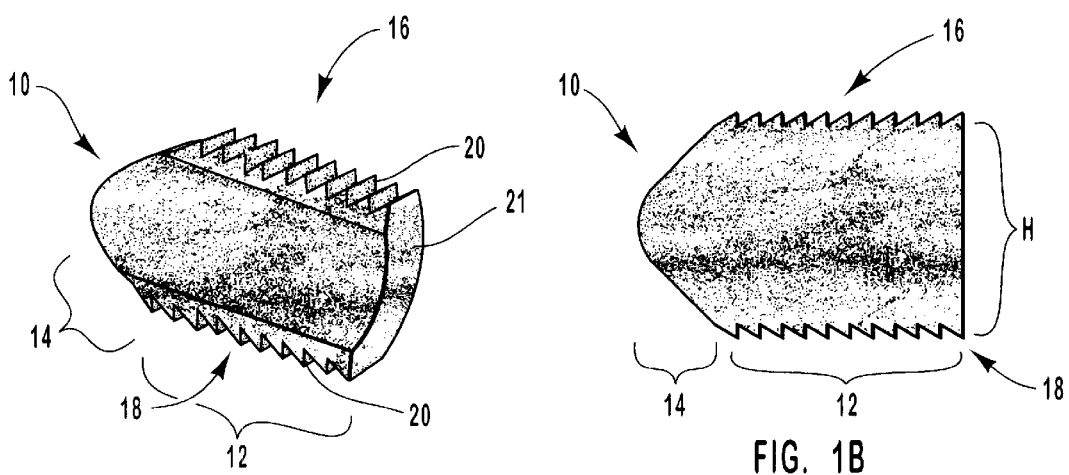
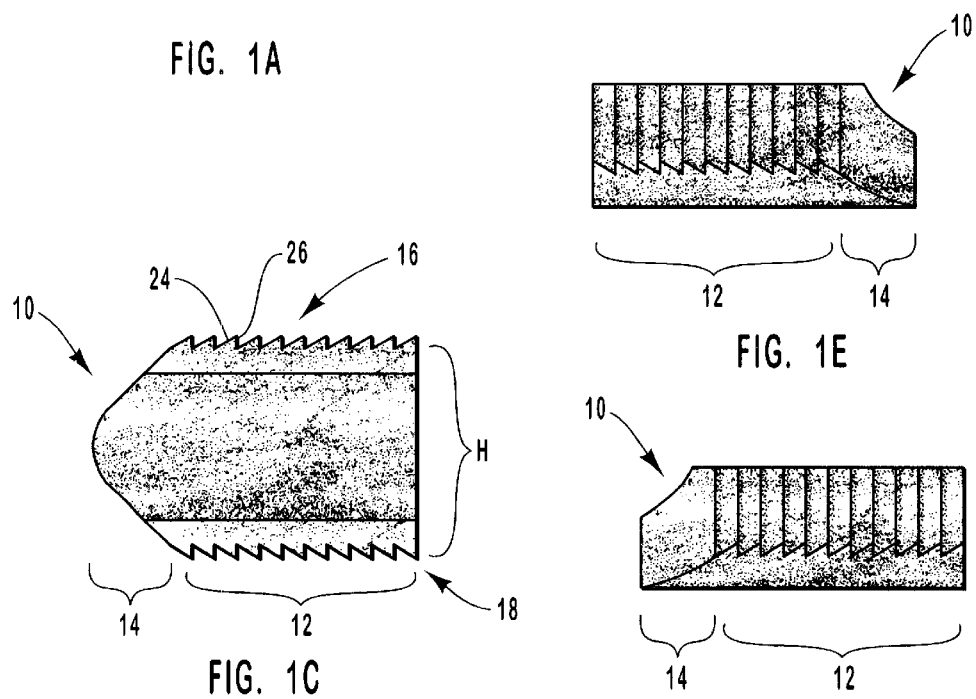
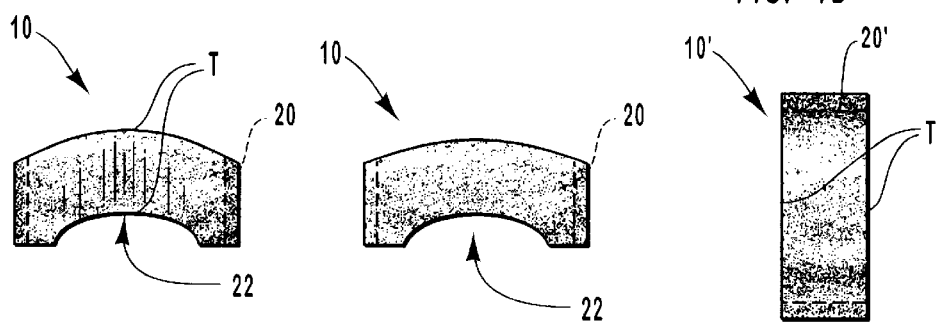

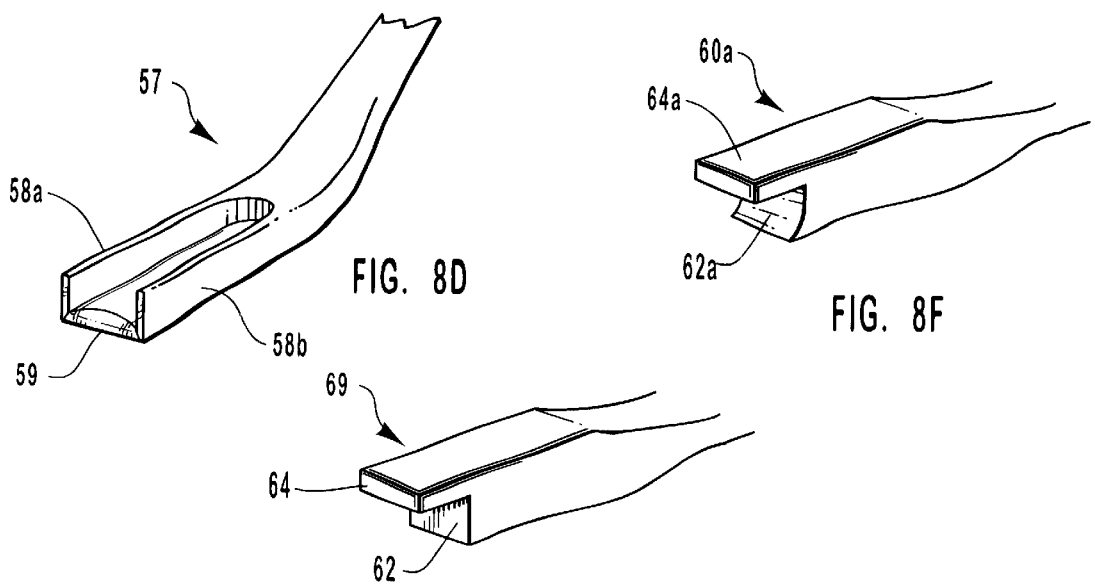
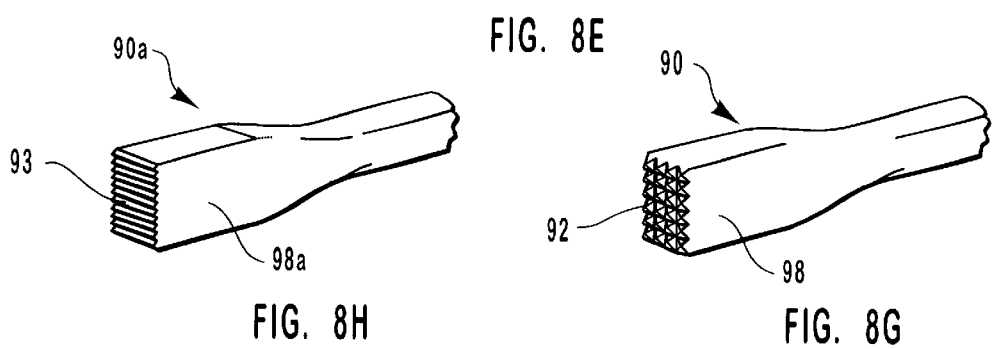
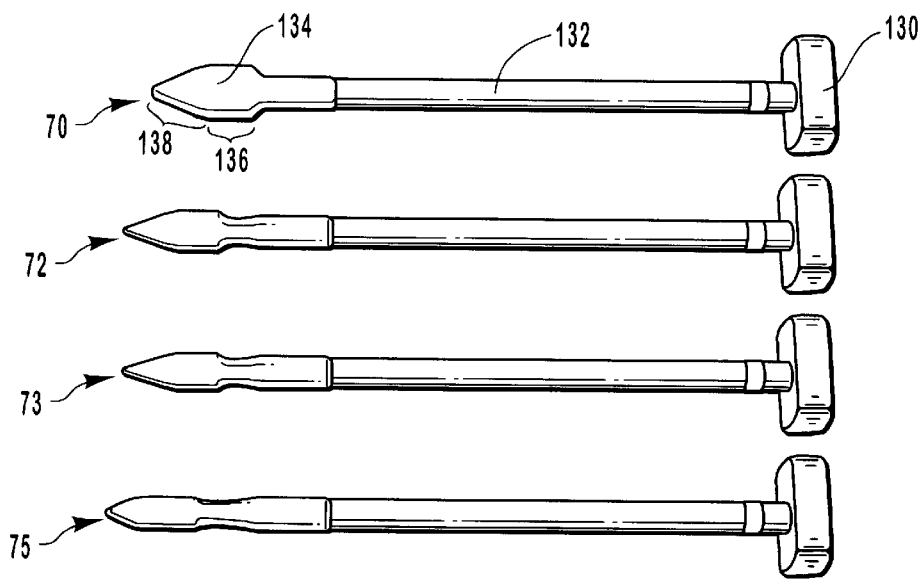
FIG. 9

SPINAL VERTEBRAL IMPLANT

BACKGROUND OF THE INVENTION

1. The Field of the Invention

This invention relates to spinal vertebral implants and methods and instruments for inserting the implants between spinal vertebrae in order to achieve spinal fusion.

2. The Prior State of the Art

When tissues between spinal vertebrae, also known as intervertebral disks, become herniated or otherwise injured, the disks can compress against nerves associated with a particular location on a spinal column. Such injuries are common in the lumbar vertebrae, for example, and can cause extreme pain to a patient suffering from such injuries.

One treatment common among medical providers to treat such injured intervertebral disks is a spinal fusion. In typical spinal fusion procedures, a portion of a vertebral disk or the entire vertebral disk is removed from between adjacent upper and lower vertebrae and the upper and lower vertebrae are fused to form a single spinal structure. The fusion of the vertebrae can alleviate the pain and discomfort associated with injured disks and frequently does not result in significant loss of bending capability.

A variety of different treatment modalities have been developed to perform such spinal fusions. Examples of typical treatments include the use of a spinal implant placed between two adjacent vertebrae. Typical implants include those made from bone, often harvested from a cadaver, for example. Following the removal of the intervertebral disk, the spinal implant is placed between the vertebrae and fuses over time with the vertebrae, eventually forming a single fused member. Typical implants can also comprise a metallic material, for example.

A variety of different approaches have been developed to use implants to achieve spinal fusion. For example, one approach employs a cage-like metallic structure in which fragments of bone are placed. The cage is mounted between adjacent vertebrae and is designed to maintain distraction between vertebrae, thus maintaining the vertebrae a desired distance apart from each other. The bone fragments foster fusion between the adjacent vertebrae. However, the cage-like structures merely act as distractors and do not fuse between the vertebrae. Instead, only the bone fragments foster fusion between the vertebrae. Thus, the space used by the cage is not used to foster bone growth and fusion. Furthermore, if bone growth does not occur through the holes for any reason, the implants merely serve as distractors, that is, placeholders that maintain spaces between adjacent vertebrae, rather then fostering fusion therebetween. The use of metal cages also introduces a foreign object into the disk space where fusion is to be obtained.

Other implants comprise harvested bone without a cage member. Typical such implants include implants comprising first and second bone pieces coupled together, for example. However, such coupled pieces can fail to fuse to each other, or can form a false joint which can eventually result in decreased fusion or the lack thereof.

There is therefore a need in the art for an improved spinal fusion implant that can be mounted between adjacent vertebrae and achieve fusion therebetween. There is also a need in the art for an improved method for placing spinal fusion implants between adjacent vertebrae. There is also a need in the art for instruments capable of achieving improved methods for implanting spinal implants.

SUMMARY OF THE INVENTION

The present invention relates to a spinal vertebral implant comprising a substantially rectangular shaped base section comprising a solid piece of bone. A nose section extends integrally from the substantially rectangularly shaped base section and preferably has a tapering shape to foster entry between adjacent vertebrae. The distal tip of the implant can be pointed or rounded, for example. The preferred nose section tapers distally and inwardly from the base section to form the distal tip portion and comprises a solid piece of bone. The implant is preferably cut from a longitudinal section of a long bone of a human cadaver.

Serrated sides assist the implant in gripping adjacent upper and lower vertebrae and in being maintained therebetween. The serrations are preferably angled in a manner that encourages the implant to be maintained between the adjacent vertebrae upon placement therebetween. The serrations grip and can impact into the adjacent vertebrae. Thus, the serrations assist in maintaining the implant tightly within the intervertebral space. First and second implants are generally placed into respective left and right sides of an intervertebral space unless the patient suffers from scoliosis or another particular condition or treatment modality applies, in which case it may be possible to use only one implant. In yet another embodiment, more than two implants are implanted, however, at least two implants are generally preferred.

A method for placing one or more implants between the adjacent vertebrae comprises forming one or more angled slots located in posterior portions of the vertebrae and configured to receive an implant. The implant is inserted into the angled slot and then further inserted between the vertebrae. Each slot is preferably formed from an upper slot portion and a lower slot portion in the respective upper and lower vertebrae. Each of these slot portions may be formed in a variety of different manners, such as by cutting or crushing a posterior portion of the edge of adjacent vertebrae. Once the implant is initially inserted into the slot, the implant can be pressed further between the vertebrae, thereby forcing a tightly inserted fit between the implant and the adjacent vertebrae.

In one embodiment, one or more slots extend from the posterior ends of the vertebrae at least approximately one third to approximately one half the distance between the anterior and posterior ends of the upper and lower vertebrae, although a variety of different configurations are available.

In one embodiment, each of the upper and lower slot portions are angled with respect to the longitudinal axis of the upper and lower vertebrae such that the placement of rectangular implants within the slots and the subsequent compression of the posterior portions of the vertebrae results in a desired level of lordosis. Through the use of the angled slots and a rectangular piece of bone, the anterior portions of the vertebrae are distracted or spread apart, thereby producing lordosis.

Instruments specifically designed to assist in the formation and ultimate configuration of the slots include, for example, (i) osteotomes designed to form a slot having a size substantially corresponding to the implant; (ii) an impactor designed to substantially mate with the proximal portion of the implant and drive the implant between adjacent vertebrae; (iii) and spacers having varying sizes that are designed to assist in enlarging the space between adjacent vertebrae and provide a space for the implant. Optionally, other instruments are employed to crush the cortical posterior bone portions. These and/or other instruments and one or more implants may form a kit for filling an intervertebral space with materials enabling fusion of upper and lower vertebrae. Other components of the kit may include bone fragments to be placed in the slots and the remaining portion of the intervertebral space to completely fill in the intervertebral space. Mechanical fixation devices such as pedicle screws and related instruments may also be used to secure the vertebrae in place and apply compression to the posterior region following the placement of the implant between adjacent vertebrae, thereby achieving and maintaining a desired level of lordosis.

The preferred longitudinally cut implant can be contacted by an instrument such as an implant impactor with significant force at a posterior end of the implant without splitting or crushing the implant. This is in part because the direction of the impact from the implant impactor is in a linear relationship with the orientation of the grain of the bone forming the implant, rather than perpendicular to the grain of the bone forming the implant.

Also in light of the use of the cut slots, the implanted implant and associated bone fragments become incorporated more readily into the spine as part of the fusion for two reasons. First, the slots offer increased surface area. Second, the cutting of the slots causes the bone to more readily fuse.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 1A illustrates a perspective view of a spinal fusion implant of the present invention;

FIG. 1B illustrates a side view of the spinal fusion implant of FIG. 1A;

FIG. 1C illustrates an opposing side view of the spinal fusion implant of FIG. 1A.

FIG. 1D illustrates a top view of a spinal fusion implant of FIG. 1A, the opposing bottom view being shown in FIG. 1E;

FIG. 1F illustrates a view of the rear (i.e., proximal) end of a spinal fusion implant of FIG. 1A with phantom lines illustrating side serrations.

FIG. 1G illustrates a view of the tapering front (i.e., distal) end of a spinal fusion implant of FIG. 1A with phantom lines illustrating side serrations.

FIG. 1H illustrates a view of the rear (i.e., proximal) end of an alternative spinal fusion implant from that of FIG. 1A that does not have a concave medullary canal portion therein.

FIG. 3 is merely a depiction for purposes of illustration only and does not show the neurological elements with the spinal canal, for example.

FIGS. 8A–9 demonstrate a series of instruments useful in a kit of the present invention as depicted in the foregoing described Figures and the discussion relating thereto.

DETAILED DESCRIPTION OF THE PREFERRED EMBODIMENTS

Figure 2:
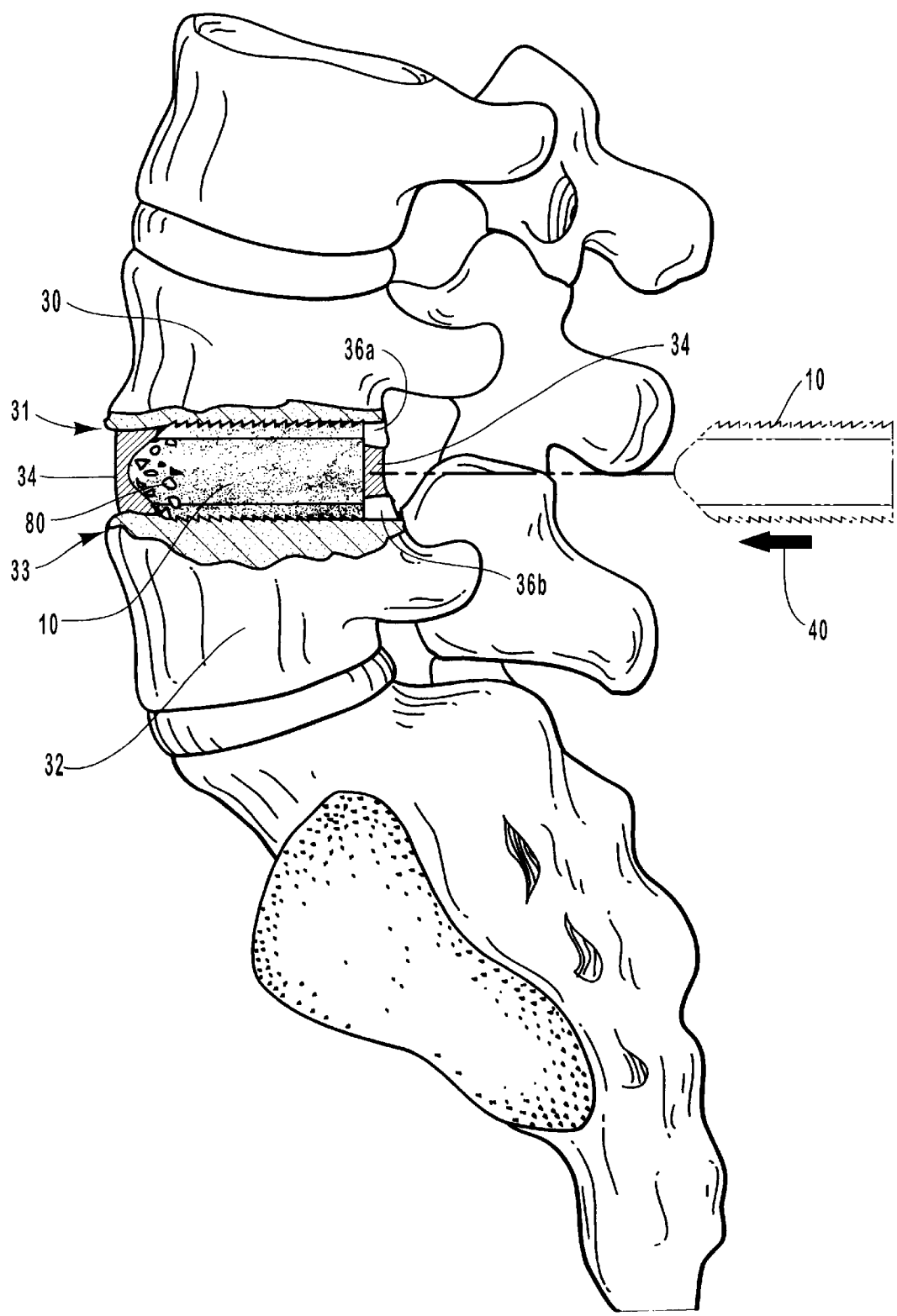
FIG. 2 illustrates the spinal fusion implant of FIGS. 1A–1F inserted between the vertebrae of a patient. A portion of a vertebral column is shown with side portions of the upper and lower vertebrae depicted in a cutaway view.

The present invention is directed generally to spinal vertebral implants that are configured to foster bone fusion between adjacent upper and lower spinal vertebrae, and methods and instruments for inserting the implants. Certain goals of the procedure include decompressing neural elements and to provide the optimum environment for fusion in a normal bone-neural configuration. This includes restoring an optimal intervertebral space height and a normal lumbar lordosis.

With reference now to FIGS. 1A–1F, an example of a spinal vertebral implant used according to the present invention will now be described. FIG. 1A shows a perspective view of an implant 10. Implant 10 has a base section 12 and a nose section 14 extending integrally from base section 12. Base section 12 preferably has a length that is greater than the height and thickness thereof. Nose section 14 has a generally tapering shape and extends integrally from the base section and tapers distally and inwardly from the base section to form a generally pointed or optionally rounded distal tip portion.

Generally, the implant 10 comprises a solid piece of bone that may be termed a "bone block". The spinal vertebral implants of the invention can generally be formed from bone blocks cut from frozen allograph femur or tibia, for example. The implants are preferably bone taken from a longitudinal section of the bone. In other words, the longitudinal axis of implant 10 is parallel to the longitudinal axis of the bone from which the implant is taken. The grain of the implant and bone is also parallel to the longitudinal axis of the bone. Consequently, as the implant is impacted into the intervertebral space with an implant impactor contacting the posterior end 21 of the implant, the implant is not damaged, but can withstand significant impact forces.

Also in a preferred embodiment, as shown, the height "H" of the implants is significantly greater than the thickness "T" thereof, allowing maximum vertebral distraction (i.e., forcing vertebrae apart from each other) with minimal nerve root retraction. This dynamic enables maximum distraction of the vertebrae without requiring the practitioner to injure nerves while inserting the implant. A cylindrically shaped implant, on the other hand, generally has the same height and thickness, requiring more nerve retraction because of the thickness of the implant and increasing the risk of nerve injury.

The implants of the present invention are driven into preformed slots in the intervertebral space to distract the vertebrae, as will be discussed in greater detail below.

Also as shown in FIG. 1A, base section 12 has first and second sides 16, 18. At least one of the sides and preferably both of the sides has a plurality of serrations 20 therein. Serrations assist the implant 10 in remaining between adjacent vertebra when driven therebetween through the use of one or more instruments as described hereinbelow. The serrations are angled to allow ready insertion in the distal, anterior direction (see arrow 40 in FIG. 2) and prevent retraction of the implant in the proximal, posterior direction. Thus, the implanted implants remain between adjacent vertebrae.

As shown in FIGS. 1F–1G, implant 10 further comprises an optional canal portion 22, extending along the longitudinal axis of the base and nose sections. Canal portion 22 is a portion of the substantially circular medullary canal of the bone from which implant 10 is harvested. It can function to provide additional space for a bone graft to form. However, canal portion 22 is not necessary to the function of the implant.

It will be appreciated by one skilled in the art in light of disclosure herein that although it is possible to use a canal 22, it is also possible to achieve the objects of the present invention without the use of a canal portion, such as by employing a flat implant 10', as shown in FIG. 1H, which demonstrates a posterior, proximal portion of an implant 10' and shows serrations 20' in phantom lines. Implant 10' has a thickness "T". For example, if the bone from which the implant 10 is harvested is sufficiently large, the canal portion 22 may be omitted entirely. In smaller bones, the presence of a medullary canal portion may be inevitable because a minimum implant thickness must be maintained.

Also as shown, in one embodiment, nose section 14 is preferably substantially shorter than base section 12. However, in another embodiment, the nose section is the same length or longer than the base section. A variety of other shapes and configurations are also possible.

Referring back to FIG. 1A, in one embodiment implant 10 preferably has a length in the range of about 20 mm to about 40 mm, more preferably about 26 mm to about 34mm, and most preferably about 30 mm; a height "H" in the range of about 8 mm to about 25 mm, more preferably about 12 to about 20 millimeters, and most preferably about 16 mm; and a thickness "T" preferably in the range of about 4 mm to about 15 mm, more preferably about 8 mm to about 12 mm, and most preferably about 10 mm. However, a variety of sizes are available depending upon the shape required for a particular procedure and the size of the patient.

Implant 10 preferably comprises a solid piece of bone. In one embodiment, implant 10 consists of a solid piece of cortical bone. Cortical bone is preferably employed because of the hardness thereof. Cortical bone is typically found in the long bones of a human cadaver, such as the human tibia and femur. Depending on the size of the cadaver from which the implant is harvested, however, other bones, such as the humerus, may also function adequately. In contrast, cancellous bone is soft and collapses under less strain.

Another aspect of the present invention is the manner in which the bone is cut from the long bone. Unlike other methods, which cut the length of an implant transversely across the femur, the present invention preferably incorporates implants that are cut longitudinally along the longitudinal axis of the femur. In other words, the longitudinal axis of implant 10 is parallel to the longitudinal axis of the bone from which the implant is cut. This method of cut has a number of advantages. First, it provides for longer implants that can be cut from the femur or other bone. Second, depending on the bone diameter and cortical bone thickness, the longitudinal cuts allow multiple bone implants to be harvested form a single cross section of a femur or other bone. Nevertheless, a variety of different types of bone and cutting methods thereof may be employed. In addition, as mentioned, impact against the posterior end 21 of implant 10 does not damage implant 10.

Thus, in one presently preferred embodiment, base section 12 and nose section 14 comprise a piece of cortical bone harvested from a longitudinal section of a bone such as the femur, for example. The bone can also be harvested from a variety of other locations, such as the tibia or humerus. Each harvested implant will generally not be identical, due to the varying nature of cadavers, and thus the shape and shading of implant 10 is merely exemplary. However, they can each be machined to achieve the desired dimensions.

There are numerous advantages to the spinal vertebral implants of the present invention. Many of the advantages derive from the shape of the implants. For example, the tapering nose 14 enables a practitioner to drive the implants 10 readily into an intervertebral space, using the nose 14 to wedge in between the adjacent vertebrae.

A further advantage of the shape is the way the serrations act as stops and grasp adjacent bone portions of the vertebrae. The serrations on upper side 16 and lower side 18 "grab" the upper vertebrae 30 and the lower vertebrae 32. This helps immobilize the implant in place, enabling a better bone fusion and increased stability. The serrations are angled with an angled portion 24 of a given serration oriented anteriorly and a flat portion 26 thereof oriented posteriorly (see FIG. 1C) to assist the practitioner in driving the implant into the intervertebral space and preventing the implant from being pressed out of the space. The serrations preferably press fit in a tight fitting relationship with adjacent upper and lower vertebrae, as shown in FIG. 2.

Another advantage is the generally rectangular shape of the implant body, which enables the implant to fit conveniently between adjacent vertebrae and enhances fusion and distraction between the upper and lower vertebrae. The tight fit of the implant body in the intervertebral space also maintains the distraction of the disc space until the fusion completes.

The implant material is advantageous in that the solid nature of the implant 10 fosters bone growth and the use of natural bone enables the implant 10 to fuse to the upper and lower vertebrae as well as to adjacent bone fragments placed within the intervertebral space to completely fill in the space with bone material. The use of bone in the fusion encourages bone growth. Bone will grow from adjacent bone sources with available blood supply. Over time, bone from the vertebrae will grow into the implant, incorporate it and completely replace the implant with a patient's bone. Thus, the implant, bone fragments placed in the invertebral space as discussed below and the upper and lower vertebrae all fuse together from the stimulated bone growth. It is an advantage of the present invention that the use of bone allows not only the bone fragments, but the bone implant itself to become incorporated as part of the final fused spine.

Further, because the implant is one solid piece, it is strong enough to be driven in and maintained between vertebrae without structural failure. Finally, bone will incorporate naturally into the bone fusion, whereas metal will not.

Figure 3:
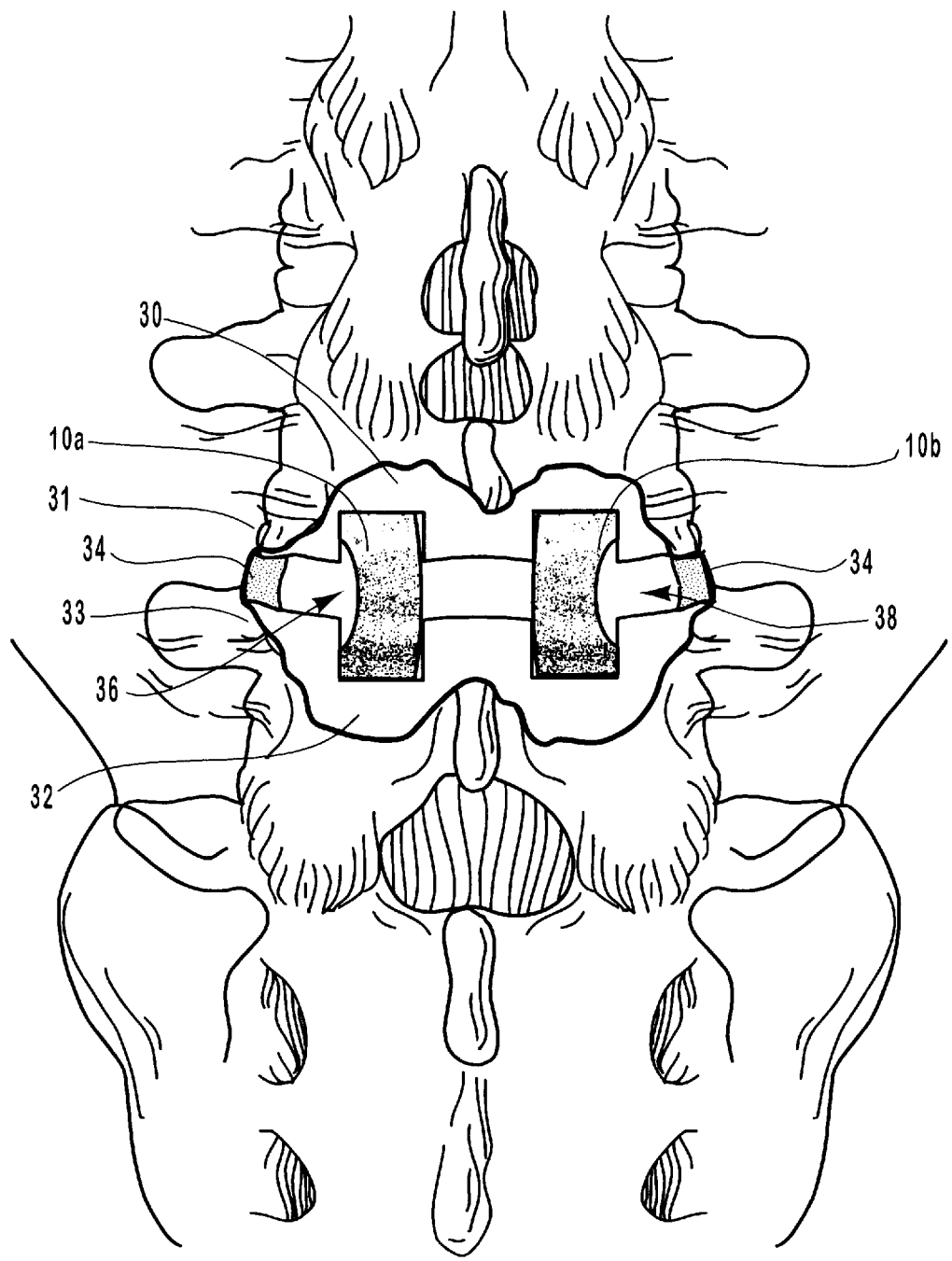
FIG. 3 depicts a cutaway, rear view of the column of FIG. 2 showing first and second spinal fusion implants inserted between adjacent upper and lower vertebrae.

With reference now to FIGS. 2 and 3, examples of placement of implant 10 will now be described. As shown, it is preferred that first and second implants 10a, 10b be placed between upper and lower vertebrae 30, 32. Side portions 31, 33 of respective upper and lower vertebrae 30, 32 are partially cut away in FIGS. 2, 5b and 5c (see hatching), in order to completely illustrate the placement of implant 10 between the vertebrae.

It is preferred to drive implant 10 between adjacent vertebrae 30, 32, such that implant 10 achieves a desired level of distraction of the anterior portions of vertebrae 30, 32. By driving nose section 14 between the adjacent vertebrae 30, 32, implant 10 is forced between the vertebrae and thereby accomplishes a tight fit therebetween, thereby fostering and encouraging greater fusion and preventing the implant from being forced out of the intervertebral space.

It is preferred that a small anterior portion of the intervertebral disc 34, known as an annulus 34 (as well as the anterior, longitudinal ligament), be left remaining between the adjacent vertebrae during the surgery such that a desired distraction is achieved and to maintain bone fragments placed within the intervertebral space. See also FIG. 6B. Annulus 34 also provides stability while the bone fragments and implants fuse in the intervertebral space. It also acts as a tension band, which maintains tension between the vertebrae and helps to immobilize the vertebrae. As shown at arrow 40, implant 10 is preferably inserted from the posterior section of the spinal column in the anterior direction. Upper and lower slot portions 36A, 36B which combine to form a single slot 36 into which implant 10 is placed are partially shown in FIG. 2.

Figure 4A:
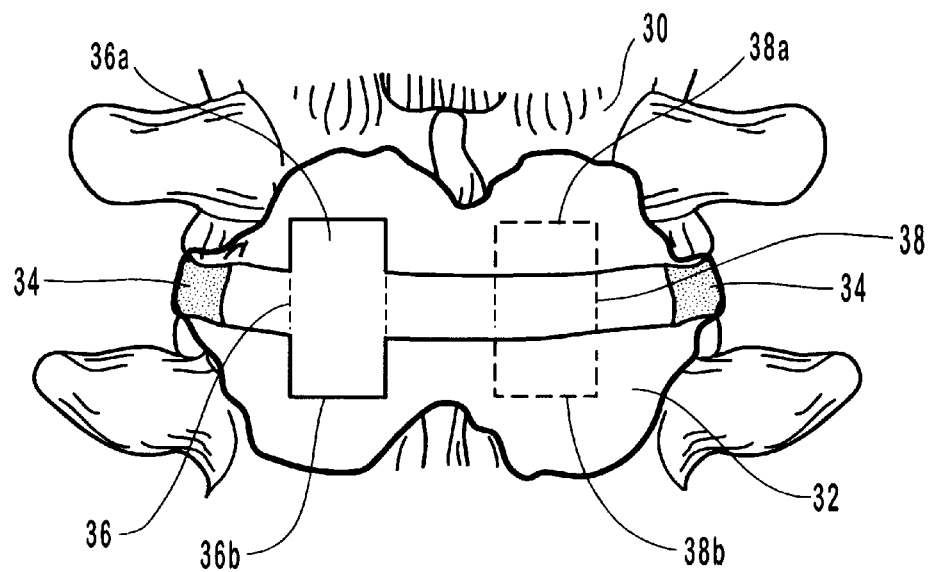
FIG. 4A illustrates the desired location of first and second slots between spinal vertebrae. The right slot is shown in a phantom view.

With reference now to FIG. 3, first and second implants 10A, 10B are shown in respective slots 36, 38 (see also FIG. 4A). In a preferred embodiment first and second implants are so maintained between the discs such that the two implants simultaneously provide fusion potential and balance the vertebrae thereon.

Also as shown in FIG. 3, the convex portion of each implant 10a, 10b is placed medially. This is advantageous because it places the smooth portion of the implant to closest to the nerve, thereby protecting the nerve. Even though preferably retracted, the nerve can slip. Thus, the smooth, convex portion is preferably placed as shown.

One method of inserting one or more implants 10 according to the present invention will now be described in additional detail hereinbelow. Only those steps that are instructive to the methods of the present invention will be discussed herein. Those procedures not discussed herein are well known in the art and do not require further discussion.

After the patient is in the surgical position and the operative portion of the spinal column is exposed, laminae and the facet joint and surrounding tissues are removed in the amount necessary to provide exposure of the neurological elements and the intervertebral disc. The intervertebral disc is excised (such as with a disk rongeur and currets), except for the anterior and lateral portion of the outer annulus. The excision is performed down to the subchondral bone of each of the upper and lower vertebrae to encourage bone growth once the implant is placed therein. Any removed bone can be kept for reuse as bone fragments as is explained in further detail hereinbelow. Attached soft tissue is removed from such removed bone and the bone is used as is or formed into smaller bone fragments for impaction into the intervertebral space.

The nerve root is retracted to allow access to the vertebral body and enable slots to be formed. The nerve root will be retracted to either side at various times in the surgery. Advantageously, the bone implant of the present invention is preferably slender (e.g., the height "H" is preferably greater than the thickness "T"), as discussed above. As a result, the nerve root does not have to be retracted very far. Thicker implants require that the nerve roots be pushed further laterally. With larger lateral movement of the nerve root, more stress is placed on the root canal. This creates a higher risk of injury to the nerve root.

As mentioned, although the intervertebral disk is preferably substantially excised, a peripheral annulus fibrosis 34, herein identified as annulus 34, is left intact. The posterior annulus is removed, but the anterior annulus remains as annulus 34. The annulus 34 provides stability while the grafts in the intervertebral space are fusing. Annulus 34 acts as a tension band to hold the anterior portion of the vertebrae in a desired position. Annulus 34 also serves to hold bone fragments in place.

With reference now to FIG. 4A–6B, an example of a method of insertion of implant 10 will be described in greater detail. As shown in FIGS. 4A and 4B, after initially removing the necessary tissues to expose upper vertebrae 30 and lower vertebrae 32, and after removing sufficient tissue from therebetween, a first slot 36 and a second slot 38 are formed in the vertebrae.

Figure 4B:
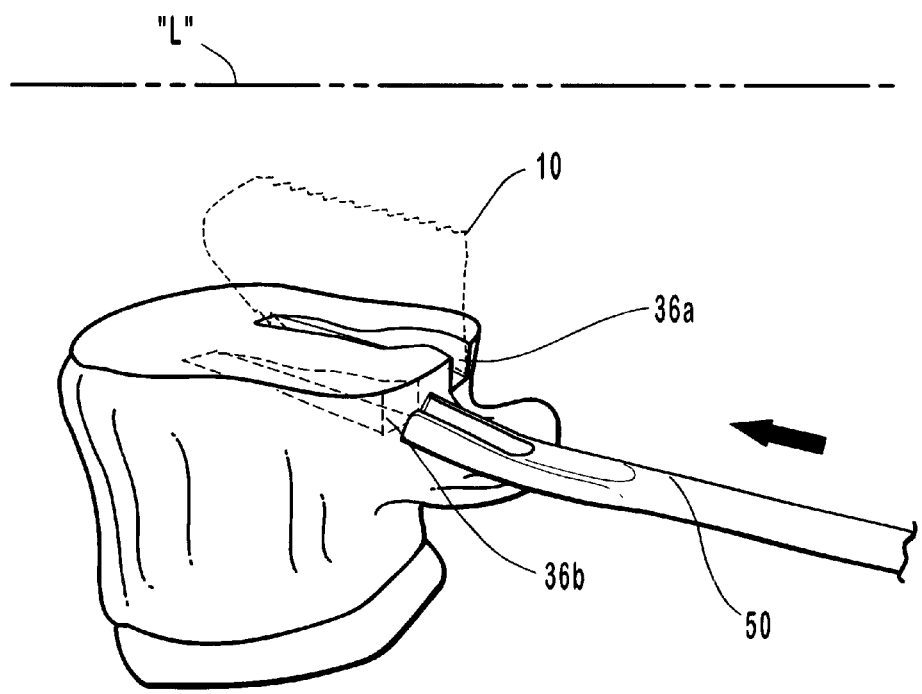
FIG. 4B illustrates the creation of first and second lower slot portions on a lower vertebra using a box osteotome of the present invention. The slot portions are cut at an angle with respect to a longitudinal axis "L" of the top portion of the lower vertebra. An example of an implant is shown in a phantom view placed in a right slot.

FIG. 4A demonstrates upper and lower slot portions 36A, 36B which combine to form a single slot 36 into which implant 10 is placed as will be discussed in greater detail hereinafter. Upper and lower slot portions 38A, 38B combine to form another single slot 38 into which another implant is placed. Slot 36 depicts a formed slot, while the phantom lines of slot 38 depict the portions of the vertebrae where cutting or impacting occurs to form the slot 38, as depicted in FIG. 4B. In a preferred embodiment, such slots are formed by forming upper and lower left slot portions 36A, 36B and upper and lower right slot portions 38A, 38B. The upper and lower slot portions together form a contiguous left slot 36 and a contiguous right slot 38.

To form the preferred upper and lower slot portions rectangular, angled slots are cut in the posterior portion of the respective vertebra, also as depicted in FIG. 4b. In one embodiment, each slots is contoured to extend from the posterior tip about one third to about one half of the length toward the anterior tip of the vertebrae. Thus, in one embodiment, the slots extend about one third to about one half of the length of the vertebrae, beginning at the posterior edge, as illustrated in FIG. 4B. Thus, in one embodiment, the slots do not extend past approximately the center of the intervertebral space. However, it will be appreciated that the slots may extend as short or as far as is required to achieve the desired distraction and lordosis with an implant therein and an even longer or shorter slot may be created (e.g., through the use of cutting tools, impacting tools, and/or spacers) in another embodiment if properly configured. The cut out portion of the bone from the posterior vertebral body can be used as bone fragments to contribute bone to the inner space, stimulate bone formation, and increase graft-vertebral body contact.

Figure 4C:
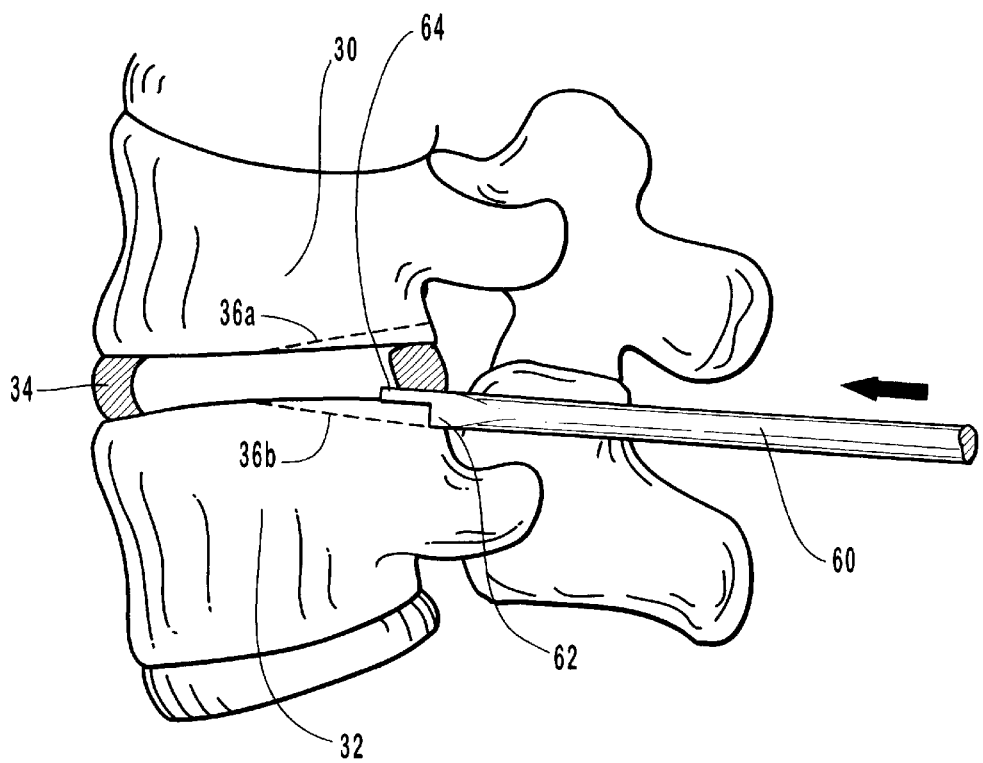
FIG. 4C illustrates the creation of upper and lower slot portions to form a collective slot using an alternative instrument of the present invention.

Slots 36, 38 serve several functions. Also as depicted in FIG. 4B and 6C, the formed slots allow insertion of a rectangular block 10 of bone while still maintaining lordosis. For example, the angled slots are formed in rectangular shape, which helps lock the implant in place. Also, the bone that is removed in forming the slot can be used in the subsequent implant procedure as described hereinafter to help stimulate bone graft. As seen in FIGS. 4B and 4C, the slots are generally angled with respect to a longitudinal axis "L" of the surfaces of the upper and lower vertebrae adjacent the invertebrael space. In addition, in the embodiment of FIGS. 4B and 4C, the anterior vertebral end-plates are not disturbed, maintaining maximal anterior end-plate strength for fixation and distraction by the implant. For example, in one embodiment, by forcing the implants through the slots and further between the non-slotted anterior portions of the adjacent upper and lower vertebrae, the anterior portions can be readily moved apart, thereby achieving lordosis upon compressing the posterior portions of the vertebrae, as shown in FIG. 6C. This dynamic will restore the normal anatomical curve, maintaining lordosis and allowing a proper fusion of the vertebral bone.

Cutting the slots also stimulates bone growth and the parallel sides of the slots provide surface area into which the posterior portion of the implant can grow. This growth stimulation and increase in surface area significantly encourages bone growth and proper fusion.

The vertebra shown in FIG. 4b preferably has a corresponding upper vertebra with corresponding slot portions. However, while it is preferred to form a slot by forming upper and lower slot portions, as shown, it is also possible to implant implant 10 through the use of a single slot portion in a single vertebra, e.g., as shown in FIG. 4b, with the other corresponding vertebra being unslotted. Thus, the term "slot" as used in this specification and the appended claims can include a slot formed from a single slot portion (e.g., upper or lower) and/or a slot formed from upper and lower slot portions, for example.

FIG. 4B shows a method of forming the slots with a tool entitled a box osteotome 50, according to the present invention. The head 57 (FIG. 8a) of this instrument has a substantially rectangular cross section and, in one embodiment, cuts a box that substantially corresponds to the thickness of an implant 10. As illustrated in the lateral view in FIG. 4B, the box osteotome 50 is placed on the posterior surface of the vertebrae, and a slot of the vertebrae is cut out. The cortical bone adjacent to the newly formed slot is left intact. The cut is from the posterior, angled towards the anterior to cut some of the cortical bone away, leaving the remaining cortical bone.

FIG. 4C shows an impacting tool 60 according to another embodiment of the invention and features the formed slots in phantom lines. Unlike the box osteotome 50, an implant impacting tool 60 does not cut into the bone. Rather, it can be used to form slots 36A, 36B, 38A, and 38B by indenting/crushing through and breaking away the bone. To indent the surface of the bone, the implant impacting tool is positioned as shown in FIG. 4C with insertion member 64 positioned adjacent to the vertebral surface that is inside the intervertebral space. An impacting member 62 of tool 60 is positioned on the lateral surface of the vertebrae. Force applied to the impacting tool breaks away the cortical surface of the vertebrae. Underlying the cortical bone surface is softer cancellous bone, which can easily be indented or broken away. The bone that is impacted or chipped off can be incorporated into the bone fusion as bone fragments.

The impacting tool 60 is particularly advantageous in that it provides a measured depth for slots 36A, 36B, 38A, and 38B. This configuration allows effective control over the depth of slot desired. Different sizes of impacting tools are obtained by varying the depth of impacting member 62. For example, the impacting member 62 can be about 4–6 mm in thickness, such that the slot is about 4–6 mm in depth, although a variety of other thicknesses and depths are available.

Figure 5A:
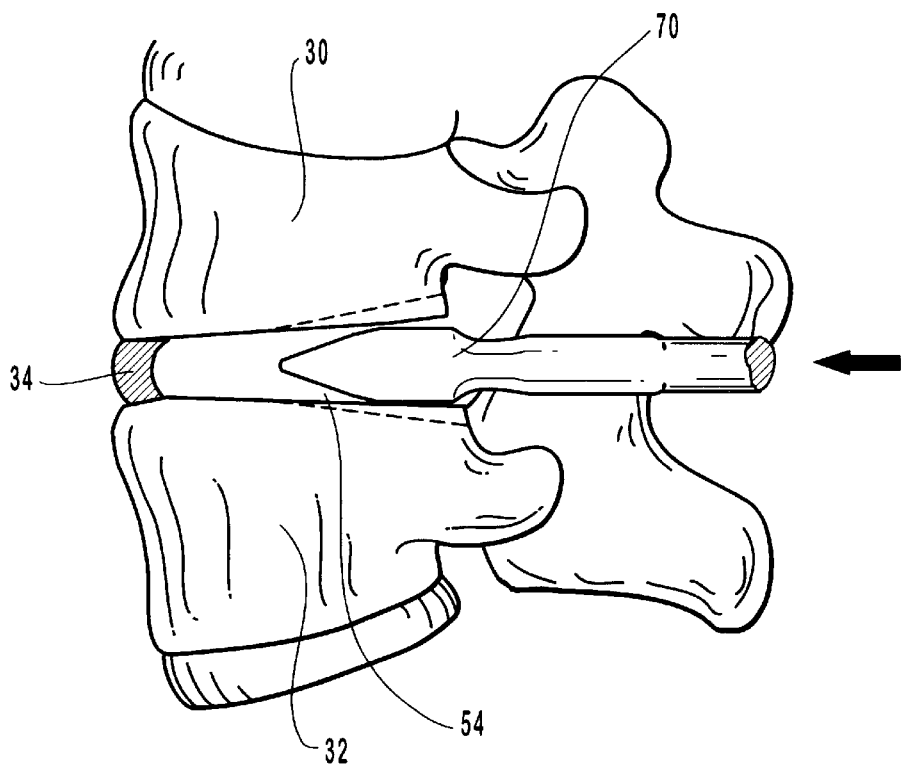
FIG. 5A illustrates the use of a spacer to create additional space between upper and lower vertebrae following the creation of the slot(s) depicted in FIGS. 4A–4C. Such space can be created through compression of cancellous bone in the upper and lower vertebrae and/or by distracting the upper and lower vertebrae.

In one embodiment, as shown in FIG. 5A, following the formation of the upper and lower slot portions to form the respective slots, a spacer tool 70 is driven into each slot, thereby fine tuning the configuration of the intervertebral space 54, such as by increasing the size of the slot. The spacer tool can create invertertebral space 54 for an implant through compression of cancellous bone in the upper and lower vertebrae and/or by distracting the upper and lower vertebrae. Spacer tools 70 of various sizes can be used sequentially to obtain the desired distraction of the intervertebral space 54 and the desired configuration of the slot. The tip of the spacer tool 70 can be shaped similarly to the tapering nose section 14 of the implant 10 of the present invention, as shown.

In one embodiment, spacers are placed into the intervertebral space 54 sequentially until the intervertebral space 54 achieves a desired height into which the implant fits. In one embodiment, a first spacer tool smaller than the desired distraction size is first driven into the intervertebral space to distract the intervertebral space to a first distance. Subsequent spacer tools can then be sequentially inserted until the space reaches the desired distraction size. In other words, beginning with the small and progressing to larger sizes, the intervertebral spacers are sequentially inserted preparing the bed for the implant until a intervertebral space is obtained according to what a pre-operative X-ray suggests the implant should be placed in.

Figure 5B:
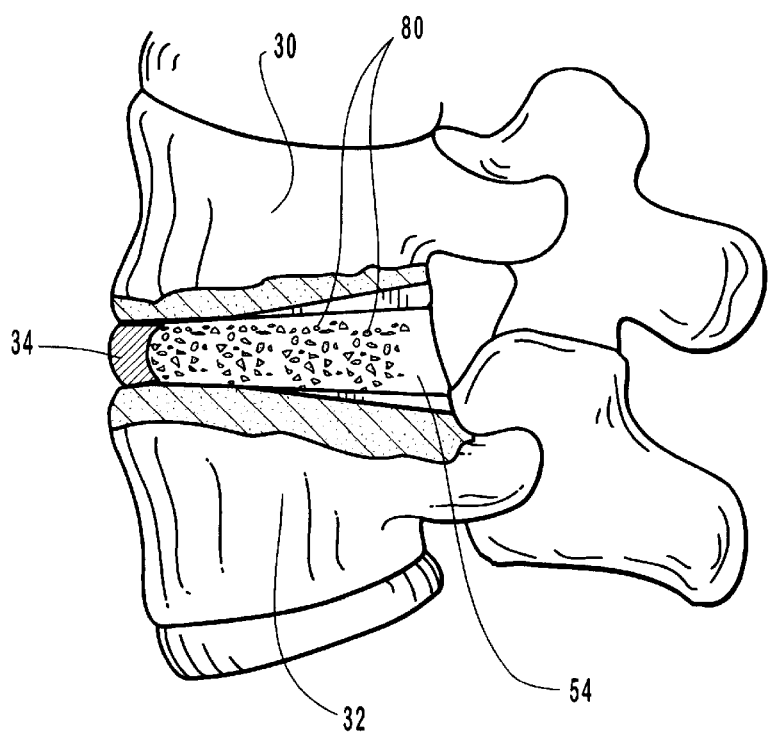
FIG. 5B illustrates the placement of additional bone fragments into the intervertebral space following the procedure of FIG. 5A.

As shown in FIG. 5B, following the spacing shown in FIG. 5A, bone fragments 80 are preferably placed into the intervertebral space 54. The bone fragments 80 serve the dual purposes of supplying support and stability to the bone implant and vertebral column during fusions and growing and incorporating into the bone fusion. It is desirable to fill the entire intervertebral space 54 with bone comprising fragments and implants. For example, following the initial distraction with the spacer tool, bone fragments from the lamina and facet joints can be ground into smaller fragments and placed in the intervertebral space. The term "bone fragments", however, as used throughout this specification and the appended claims shall include any bone material that is capable of being fit into the intervertebral space, such as bone chips, bone pulp, or other fragments of bone, for example.

Figure 5C:
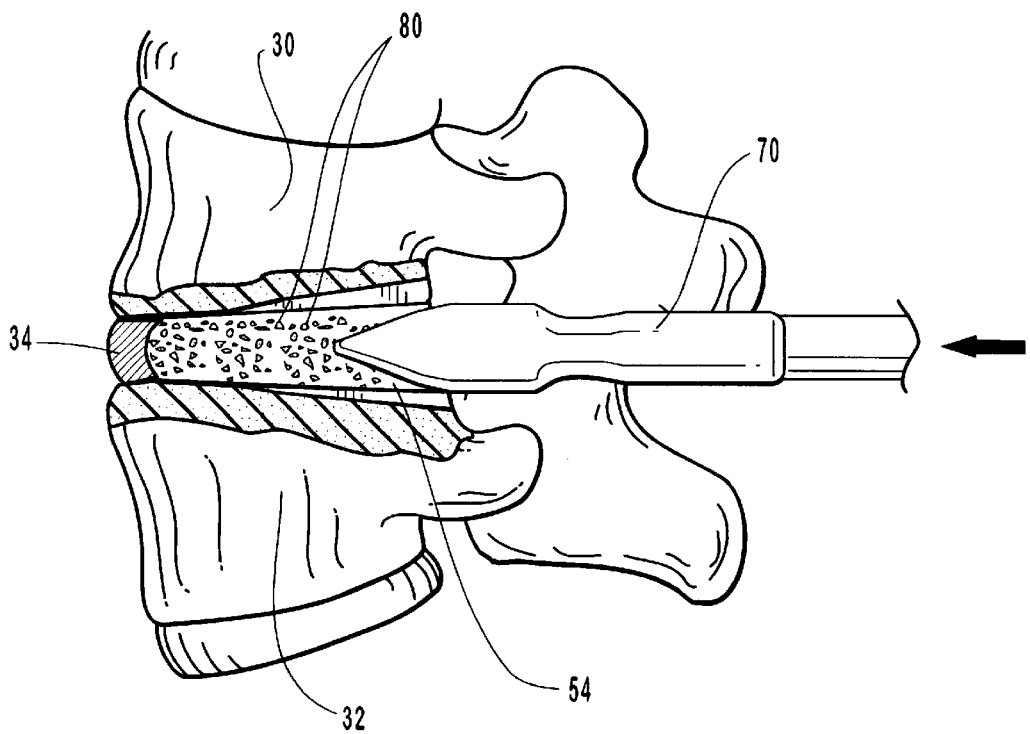
FIG. 5C illustrates the placement of a spacer into the intervertebral space following the procedures of 5A and/or 5B.

A sufficient quantity of bone fragments 80 are placed in the intervertebral space to surround the implant and fill the space following impacting as described hereinafter. This ensures bone growth throughout the space as well as adequate support and stability. After packing the intervertebral space with bone fragments 80, spacer tools 70 can be reinserted, as shown in FIG. 5C to impact and spread the graft and create a space for the implant. The process of filling in the intervertebral space with bone fragments 80, then placing the spacer therein can be continued until the space if filled with fragments but retains a space for the implants, as illustrated in FIG. 6B.

Additional bone fragments can be obtained, for example from the iliac crest bone or any extra bone obtained from the spinus or facets during other stages of the surgery. One of skill in the art will appreciate in light of the disclosure herein that materials are regularly developed and may serve as adequate "bone fragments" of the present invention, provided they function to promote bone fusion and provide the requisite strength. For example, a bone morphogenic protein may provide a suitable material to serve as "bone fragments" of the present invention.

Figure 6A:
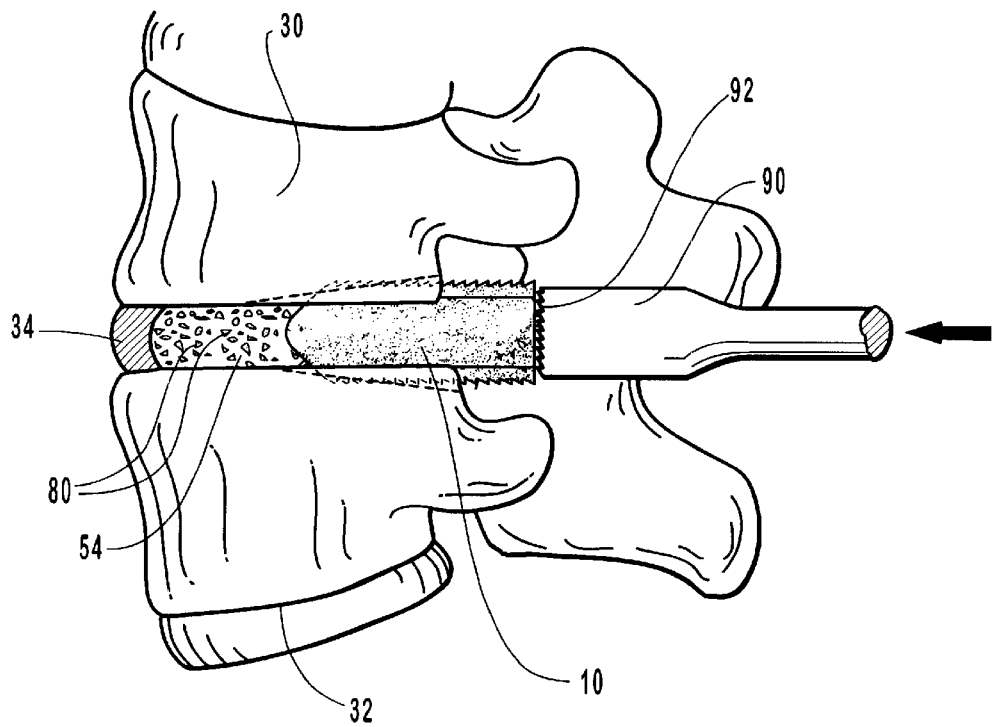
FIG. 6A illustrates the insertion of the spinal implant of FIG. 1A–1F using an impactor of the present invention.

With reference now to FIG. 6A, following the placement of the bone fragments into the slot, each implant is preferably driven into each slot 36, 38 through the use of an implant impactor 90. The implant impactor 90 has a rectangular shape that substantially corresponds with the proximal, posterior surface 21 of implant 10 and substantially corresponds to the size of the slot into which the implant is to be placed. The rectangular tip has a plurality of spikes 92 to ensure it does not slip off the implant during impacting.

Figure 6B:
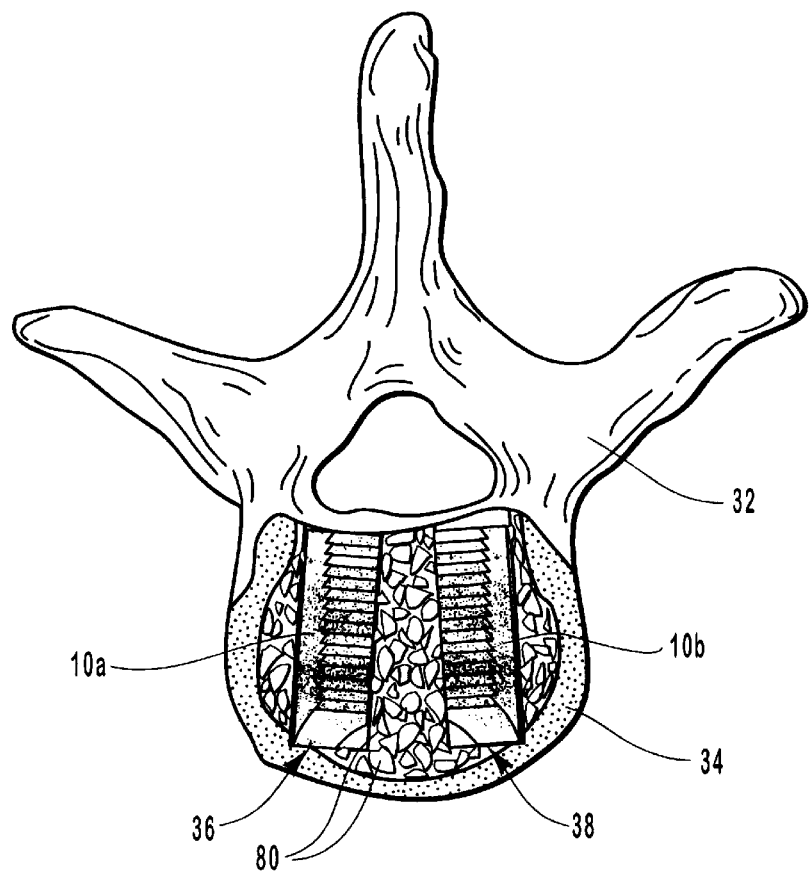
FIG. 6B illustrates first and second inserted spinal fusion implants with bone fragments shown surrounding the inserted implants in a cross sectional view of a vertebral column to fill the intervertebral space with bone material comprising bone fragments and implants.
Figure 6C:
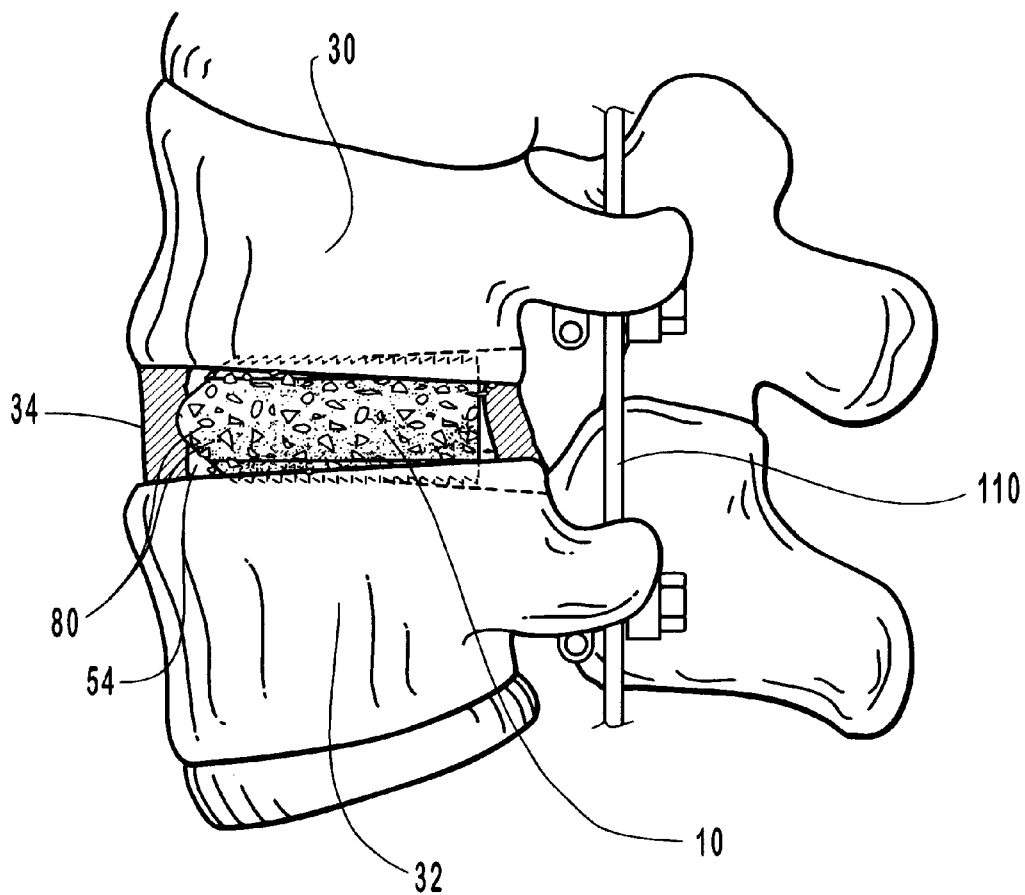
FIG. 6C illustrates upper and lower vertebrae with an implant therebetween in a manner that achieves a desired lordosis by mounting a proximal portion of the implant in posterior slot portions, mounting a distal portion of the implant in an anterior portion of the intervertebral space and affixing a mechanical fixation device to posterior portions of the vertebrae to achieve posterior compression.

In one embodiment, implant 10 is driven past the location of the slot and adjacent the anterior annulus 34, as shown in FIGS. 6b and 6C. The implant is placed in the intervertebral space and aligned with the corresponding slot. The implant is then impacted into the space and, in one embodiment, is seated 2 mm to 3 mm past the posterior vertebral body cortex of the adjacent vertebra. For example, in one embodiment, the distal tip of the implant 10 is driven approximately 3 mm from the distal tip of annulus 34, while the proximal tip of implant 10 is approximately 2–3 mm from the proximal end of the intervertebral space.

In the case of multiple disc replacements, the procedure is repeated for all intervertebral spaces on one side before going to the other side. Patients with scoliosis can be treated by inserting an implant only on the concave side with bone fragments filling the space on the convex space side. As illustrated in FIG. 6B, the bone fragments 80 are compacted in the intervertebral space and spread around the implant 10.

In addition, as shown in FIG. 6C, upon placing implant 10 far enough into the intervertebral space, annulus 34 tightens and the anterior portions of the vertebrae distract.

With continued reference now to FIG. 6B, an overhead view of an example of first and second implants driven into first and second respective slots 36, 38 is shown. As shown, implants 10A, 10B are driven between neighboring discs such that a balance is achieved fostering proper distraction and fusion.

Upon driving implant 10 into the desired space, lordosis is maintained in a desired amount by mechanically compressing the posterior portions of the vertebrae, and maintaining the vertebrae in the compressed position, such as through the use of a mechanical fixation device 110, as depicted in FIG. 6C.

For example, after the implantation is complete, the vertebral column can be mechanically fixed in position with screws to obtain the desired lordosis as discussed in U.S. Pat. Nos. 5,947,965 to Bryan entitled SPINAL FIXATION APPARATUS AND METHOD, U.S. Pat. No. 5,676,665 to Bryan entitled SPINAL FIXATION APPARATUS AND METHOD, U.S. Pat. No. 5,498,262 to Bryan entitled SPINAL FIXATION APPARATUS AND METHOD, and U.S. Pat. No. 5,306,275 to Bryan entitled LUMBAR SPINE FIXATION APPARATUS AND METHOD, the disclosures of each of which are incorporated herein by reference. In one embodiment, a portion of the pedical screw procedure is started before the implant is implanted, after which the procedure is completed. For example, for convenience pedical pins (placed preliminary to placing screws) may be placed in the positions desired while the practitioner is working on a particular side of the intervertebral space before implantation. The screws may then be placed in the desired positions following implantation, for example. Optionally, no pedical pins are used preliminary to the use of screws.

The mechanical fixation devices may optionally be removed at any time after the fusion is complete, but such removal is not necessarily required.

Figure 7A:
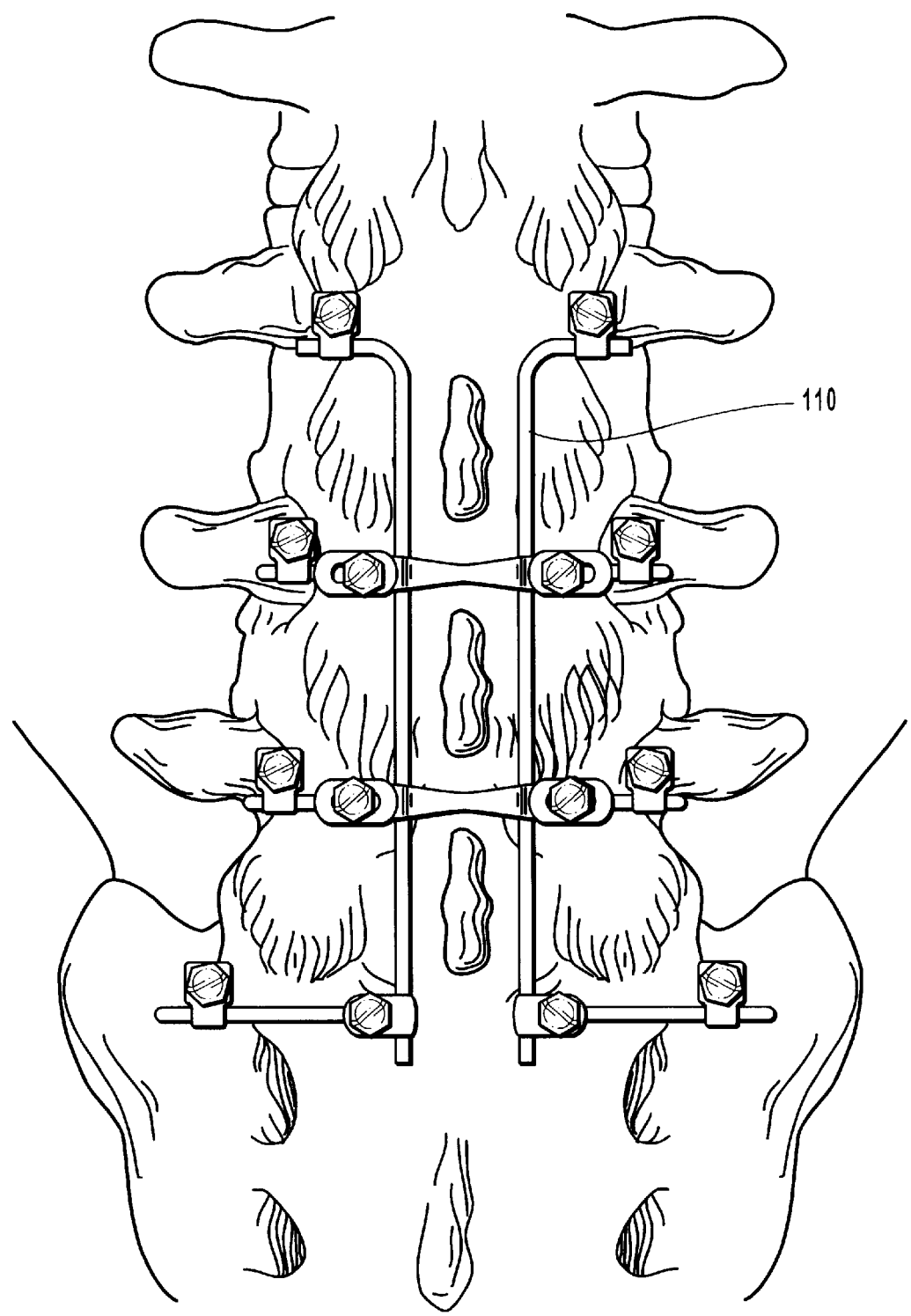
FIG. 7A demonstrates the final coupling of a mechanical fixation device to the spinal column to maintain the desired compression of vertebrae in place following the placement of implants between multiple vertebrae.
Figure 7B:
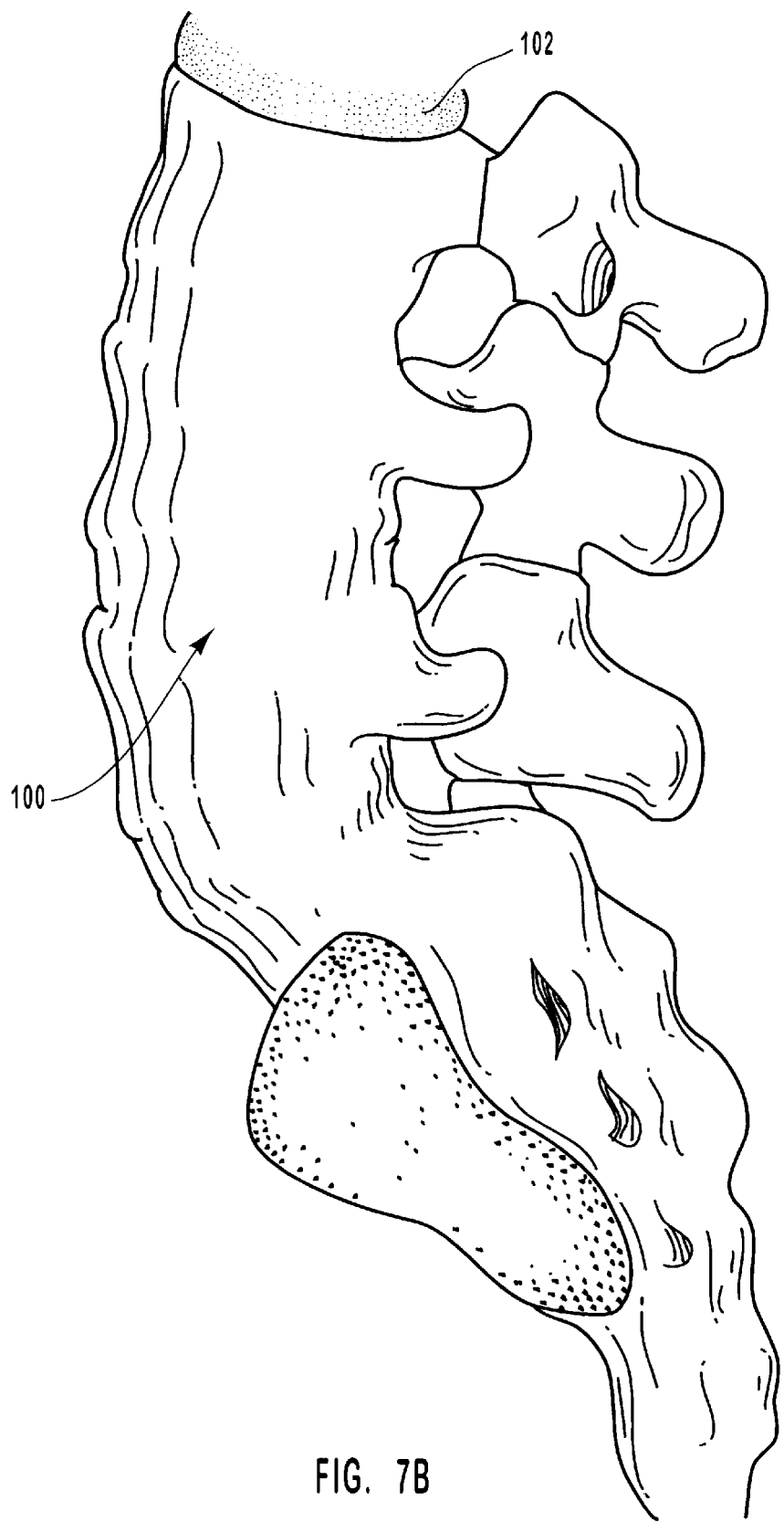
FIG. 7B demonstrates a variety of fused vertebrae, as can be achieved through the use of the system, method and tools demonstrated in FIGS. 1–7A.

With reference now to FIG. 7a, upon tightening the mechanical fixation device 110, the posterior portions of the upper and lower vertebra are compressed, thereby increasing the tension in annulus 34 and maintaining a desired level of lordosis. With reference now to FIG. 7b, following a certain amount of time, the upper and lower vertebrae fuse together and the bone fragments and implanted implants fuse, thereby forming a solid bone member 100. Bone member 100 has received fusion at three levels (i.e., three intervertebral spaces fused), with an upper disk 102 remaining. The solid bone member is now free from disruptive, herniated, or injured discs, is convenient and practical for a patient, and often delivers the patient from significant pain without immobilizing or significantly reducing the mobility of the patient. Despite the slight loss of spinal flexibility due to the spinal fusion, a patient's overall mobility is often not significantly impaired. This is due to the relatively small import of the spinal column relative to the hip and other joints in overall flexibility.

Figure 8A:
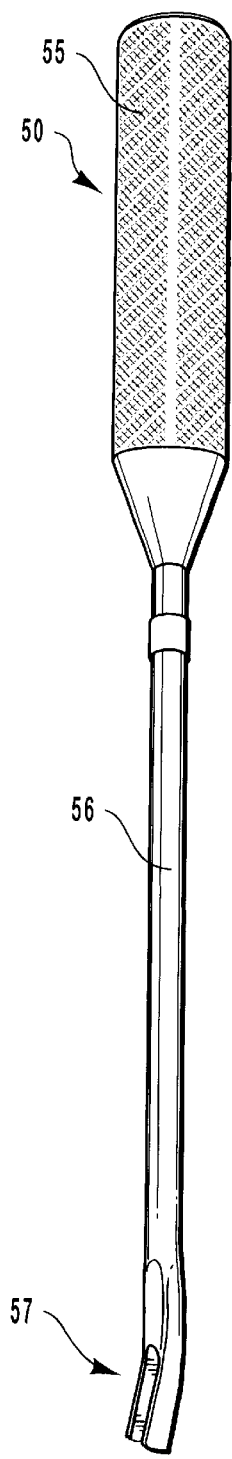

Referring now to FIGS. 8A–9, the present invention also encompasses a variety of instruments used to implant the intervertebral implant discussed hereinabove. The box osteotome 50 discussed hereinabove may be structured as illustrated in FIGS. 8A and 8D. It is comprised of a handle 55, a neck 56 coupled to handle 55, and a head 57 coupled to neck 56. Head 57 comprises a scraper having first and second longitudinally extending side members 58a, 58b that couple transversely to a longitudinally extending body member 59. The distal edges of the longitudinally extending members 58a, 58b, and 59 can be sharpened to facilitate cutting upper and lower slot portions. In another embodiment, the edges are blunt, thereby assisting in crushing the bone. The thickness of body member 59, and consequently the distance between side members 58a and 58b may correspond generally to the thickness of implant 10, thereby cutting the desired slot configured to fit the implant therewithin. Thus in one embodiment, head 57 substantially corresponds to the thickness of the implant (i.e., has substantially the same thickness as the implant).

Head 57 has a substantially rectangular cross section. Head 57 is configured to form a rectangular slot. In one embodiment, head 57 extends slightly outwardly as it moves away from the neck portion. Head 57 is configured to cut portions of the posterior portion of the bone away and/or to crush portions of the posterior bone.

Figure 8B:
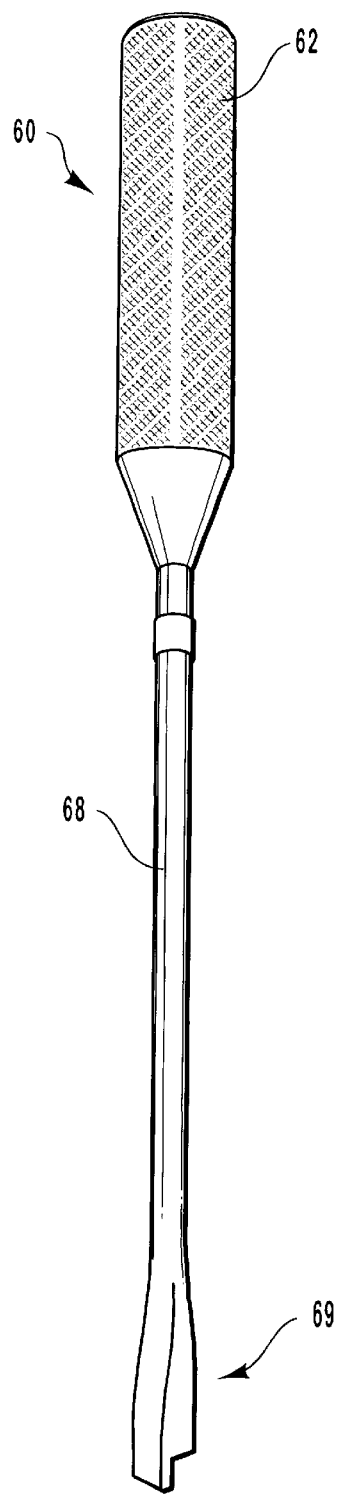

As mentioned above, alternatively, slots 36, 38 can be formed by crushing or impacting rather than cutting. Referring to FIGS. 8B, 8E, an impacting instrument 60 of the present invention is comprised of a handle 62, a neck 68 coupled to the handle 62, and a head 69 coupled to neck 68. As illustrated in FIG. 8E, head portion 69 of impacting instrument 60 is comprised of an impacting member 62 and an insertion member 64 perpendicular to said impacting member 62. To indent the surface of the bone, the impacting instrument is position as shown in FIG. 4C with insertion member 64 positioned adjacent to the vertebral surface that is inside the intervertebral space. The impacting member 62 is positioned on the posterior surface of the vertebrae. Force applied to the impacting instrument 60 breaks away the cortical surface of the vertebrae. Underlying the cortical bone surface is softer cancellous bone, which can also easily be indented or broken away.

This configuration of impacting instrument 60 allows effective control over the depth of slot desired, as discussed above. Different sizes of impacting instruments are obtained by varying the depth of impacting member 62. For example, the impacting member 62 can be 4–6 mm in depth, although a variety of other configurations and sizes are available.

As seen in FIG. 8F, in an alternative embodiment of an impactor head 60a, the head comprise an insertion member 64a and an impacting member 62a having a sharpened lip that can also be used for cutting.

Figure 8C:
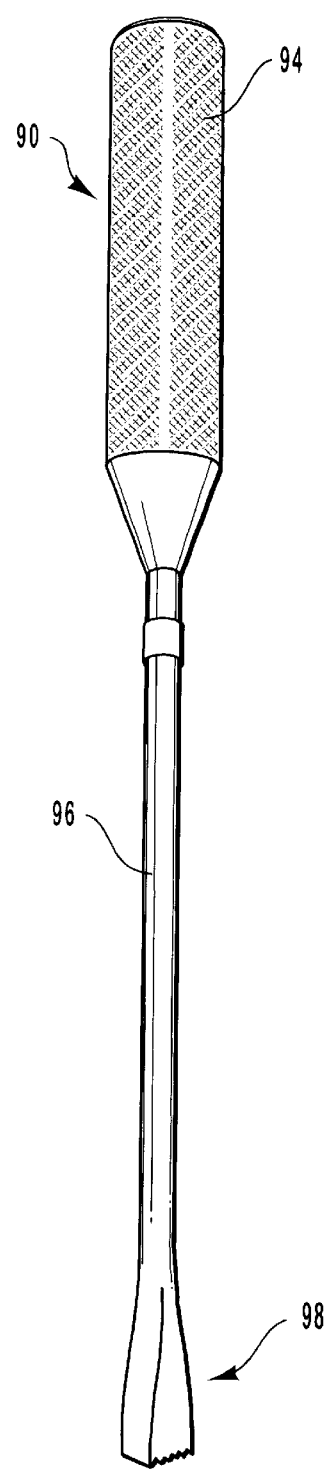
Figure 8A:
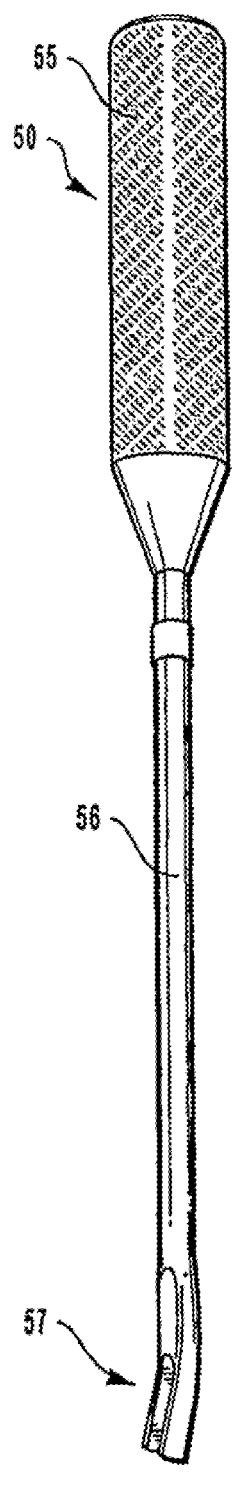
Figure 8B:
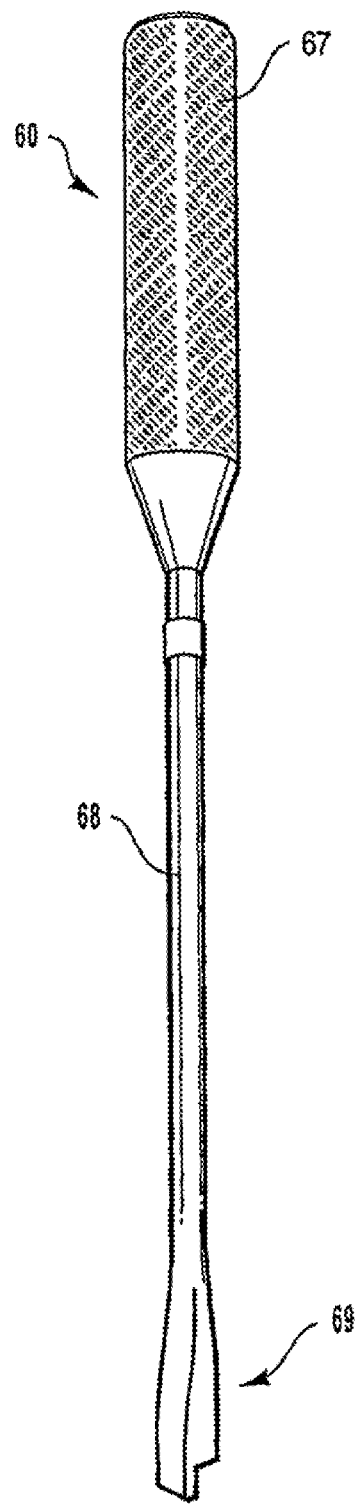
Figure 8C:
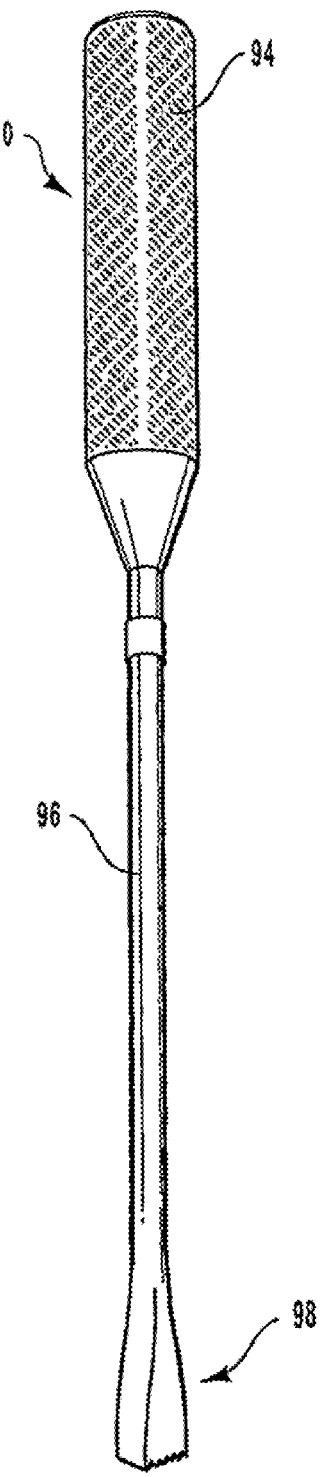

Referring now to FIGS. 8C and 8G, an implant impactor 90 according to the present invention is comprised of a handle 94, a neck 96 coupled to handle 94, and a head 98 coupled to neck 96. As illustrated in FIG. 8G, head portion 98 of the impacting instrument 90 has a generally rectangular shape and a plurality of spikes 92 thereon. Optionally, corrugations or grooves 93 may be substituted for spikes as shown in the alternative head 98a of an implant impactor 90a, shown in FIG. 8H. Implant impactor 90 is used to force implant 10 into slots 36, 38 formed in the vertebrae. Spikes 92, corrugations, or grooves 93 assist in gripping implant 10 as it is being forced into the slots. Such spikes 92, grooves 93 or corrugations are examples of means for enhancing the gripping surfaces of the heads. One skilled in the art will recognize, in light of the disclosure herein, that other gripping means can be employed to grip the implant.

In one embodiment, head 98 of impactor 90 substantially corresponds to the height and thickness of implant 10 (i.e., has a substantially similar height and thickness), such that impactor 90 can effectively force implant 10 through a slot substantially corresponding to the height and thickness of the implant without creating a larger slot.

Referring now to FIG. 9, spacing instruments 70, 72, 73, and 75 are each comprised of a handle 130, a neck 132 coupled to the handle, and a head 134 coupled to the neck 132. The head portion 134 has a body portion 136 and a nose section 138 tapering inwardly and distally away from the body portion to form a generally pointed or rounded tip portion at a distal end thereof, substantially similar to implant 10. As is illustrated in the figures, the head portion 134 of each spacing instrument has a different thickness.

The spacers can thus be used sequentially to distract adjacent vertebrae and increase the height of the slots 36, 38. In one embodiment, the head of the final spacing tool used in the sequence is slightly smaller than the implant, such as about 2mm smaller in height than the height "H" of the implant, for example, such that the spacers substantially create a space for the implant, but such that the implant is press fit in a tightfitting relationship between the adjacent vertebrae.

Nevertheless, as shown in the tools of FIG. 9, in one embodiment, even if the head of the spacer is slightly smaller, the spacer still has a shape substantially similar to the implant such that the spacer creates a space sufficient for the implant to be implanted into.

In one embodiment, the spacers can crush some of the cancellous bone in the intervertebral space, such as in the posterior portion and/or approximately the middle of the intervertebral space (and even in the anterior portion in certain embodiments), thus fine tuning the slot in the intervertebral space. In one embodiment, the implant is pressed past the middle of the intervertebral space, press fitting into the cancellous bone in the space and contacting the anterior, cortical bone and thereby distracting, i.e., pushing apart the anterior peripheral portions of the adjacent vertebrae.

The instruments described in FIGS. 8 and 9 may be manipulated in a variety of different manners, such as by being held by a practitioner and/or contacted with a mallet or hammer, for example, to derive the force necessary to perform a particular procedure, as will be appreciated by one skilled in the art in light of the disclosure herein.

Another aspect of this invention is a system including one or more of the hereinabove described instruments, one or more vertebral implants 10, and, optionally one or more bone fragments.

The following example is given to illustrate one possible embodiment of the present invention, and is not intended to limit the scope of the invention.

EXAMPLE 1

The following procedure was effectively performed on a patient. A midline incision was made and the patient's spine was exposed by subperiosal dissection. Decompression was begun with partial facet joint excision. The capsule of the facet joint was removed with electric cautery and periostial elevator. Since virtually all removed bone is preferably used as graft, extra time was taken to meticulously remove attached soft tissue. The upper facet was cut transversally with an osteotome and removed. Initially, the spinous processes were left intact to facilitate distraction with the laminus spreader.

The interspinous ligament was removed and a laminae spreader was inserted. Cartilage and other soft tissue from the facet joint were removed with a cob elevator and an adison rongeur. The inferior facet was excised, saving the small bits of bone for later grafting. The disk space was radically excised to the outer annulus. The end-plates were vigorously curetted to bone. A cottonoid was placed, the laminae spreaders removed, and the decompression procedure was performed at each of the other levels for which fusion was desired, all on the same side.

The transverse process was cleaned of soft tissue and the transverse process retractor was placed. Sleeves of the pedicle burr were placed over the transverse process and the pedicle entry point was burred. A small diameter pedicle reamer was placed in the burr crater and pushed down the pedicle with back and forth motions. A larger reamer was then inserted.

A C-clamp trial confirmed the C-clamp would fit close to bone lateral to the facet joint. The superior facet joint (i.e., the portion above the level of the fusion) was not violated. A pedicle pin was inserted. The inferior pedicles were reamed under direct vision. The medial wall was palpated with a nerve hook. Burring and reaming were performed in the usual manner. After inserting the reamer and the pins, repeat palpation with the nerve hook confirmed correct pedicle reaming.

Burring, reaming and pin insertion were accomplished on the same side for the remaining pedicles to be instrumented. The same procedure was then performed on the other side.

After all levels had been decompressed and pedicle pins placed, the laminus spreader was reinserted and the nerve roots retracted. Notches were cut in the posterior portion of each vertebral body. Beginning with a small height and progressing to larger heights, the intervertebral disk spacers were sequentially inserted preparing the bed for the implant. Bone from the lamina and facets were ground into bone meal and placed in the disk space. Spacers were reinserted to impact the bone and recreate the bed for the implant.

The implant was impacted into the space and seated two to three millimeters below the posterior vertebral body cortex. The procedure was repeated for all disk spaces on one side before going to the other side. (Patients with scoliosis can be treated by inserting a implant on the concave side, and bone fragments only on the convex side.)

A final inspection of the spinal canal and nerve roots was performed. The foot of the bed was elevated to assist in restoration of lordosis prior to instrumentation. Instrumentation began with the upper pedicle. A depth gauge was inserted to palpate the pedicle wall and determine the screw length. A construct comprising an L-rod held with a locked stem clamp, other stem clamps as needed and a C-clamp with a C-clamp holder was assembled. The measured pedicle screw was inserted through the C-clamp and placed into the pedicle. The C-clamp was pushed down to its final resting position close to bone and lateral to the facet.

The screw was then inserted. The screw was tightened to prevent medial/lateral translation, but not rotation of the L-rod on the C-clamp. The upper facet joint was not disturbed. A C-clamp was then placed on the inferior stem clamp, the stem clamp holder was removed, the pin in the pedicle was removed and reinserted through the C-clamp and down into the pedicle. The pin was then removed, the depth gauge measurement to the anterior cortex of the sacrum was obtained, and then the screw was inserted. The screw could then perfectly engage the anterior cortex of the sacrum, obtaining bi-cortical fixation without need for x-raying.

Lordosis can be increased by shortening the distance between the upper and lower screws producing normal, physiological extension with vertebral rotation. The superior and inferior screws were loosened and an upper stem clamp was secured to the rod by tightening the screw. Compression was applied between the stem clamps and the bottom stem clamp screw was tightened. The upper and lower screws were then tightened to lock the construct into its final position.

Another method of restoring lordosis is to use angled lordodic rods. The rods can be placed in the superior and inferior screws, compressed together and the inferior stem clamp screw can then be tightened. The middle pedicle screws can then be inserted easily regardless of pedicle orientation.

Cross-plates were then applied. These could be applied at multiple levels without the need for added connectors to the rod. A final tightening of all screws was then performed. An iliac crest bone graft was obtained by raising a skin-and-subcutaneous-flap over the right ileum. This bone was harvested and then packed under direct division along the transverse processes and the lateral wall of the pedicles. Any extra bone obtained from spinus processes or facets was ground into a mesh and impacted laterally. A final inspection of the spinal canal and nerve roots was then accomplished. The wound was closed in the usual manner, and prophylactic antibiotics were administered for 48 hours. An abdominal binder was used. No rigid brace was required.

This example illustrates one embodiment of the present invention although a variety of other procedures and methods can be employed according to the present invention.

Embodiments of the present invention are also disclosed in copending U.S. Patent Applications entitled "Spinal Vertebral Implant and Methods of Insertion" to Donald W. Bryan, filed Sep. 15, 2000, which is incorporated herein by reference and "Instruments for Inserting Spinal Vertebral Implant" to Donald W. Bryan, filed Sep. 15, 2000, which is incorporated herein by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which comes within the meaning and range of equivalency of the claims are to be embraced within their scope.

What is claimed and desired to be secured by United States Letters Patent is:

1. A spinal vertebral implant configured to foster bone fusion between upper and lower adjacent spinal vertebrae between which the implant is placed pursuant to a spinal surgical procedure, the spinal vertebral implant comprising:
   a longitudinal axis;
   a solid piece of bone having a grain oriented parallel to the longitudinal axis of the implant, comprising:
      a substantially rectangular shaped base section; and
      a tapering nose section extending integrally from the substantially rectangular shaped base section.

2. An implant as recited in claim 1, wherein the nose section tapers distally and inwardly from the base section to form a generally pointed distal tip portion, the nose section comprising a solid piece of bone.

3. An implant as recited in claim 1, wherein the nose section tapers distally and inwardly from the base section to form a generally rounded distal tip portion, the nose section comprising a solid piece of bone.

4. An implant as recited in claim 1, wherein the implant has a height and a thickness, and wherein the height of the implant is substantially greater than the thickness of the implant.

5. An implant as recited in claim 1, wherein the implant has a length and a height, and wherein the length of the implant is greater than the height of the implant.

6. A spinal implant as recited in claim 1, wherein the implant comprises cortical bone.

7. A spinal implant as recited in claim 1, wherein the implant comprises a longitudinal section from a long bone selected from the group consisting of the tibia and the femur.

8. A spinal implant as recited in claim 1, further comprising a canal region along the longitudinal axis of the implant.

9. A spinal implant as recited in claim 1, wherein the implant has a flat cross section.

10. A spinal implant as recited in claim 1, further comprising a plurality of serrations on at least one side of the implant.

11. A spinal implant as recited in claim 10, wherein the serrations are oriented such that an angled portion of at least one serration is oriented anteriorly and a flat portion of the serration is oriented posteriorly.

12. A spinal implant as recited in claim 10, wherein the serrations are angled in a manner that encourages the implant to be maintained between adjacent vertebrae.

13. An implant as recited in claim 1, wherein:
   the rectangular shaped base section comprises a top side and a bottom side;
   the top side and the bottom side are substantially rectangular surface areas;
   the top side and the bottom side are substantially coplanar; and
   at least one of the top side and the bottom side comprise a plurality of serrations thereon.

14. A spinal vertebral implant configured to foster bone fusion between upper and lower adjacent spinal vertebra between which the implant is placed pursuant to a spinal surgical procedure, the spinal vertebral implant comprising:
   a longitudinal axis;
   a solid piece of bone having a grain oriented parallel to the longitudinal axis of the implant, comprising:
   a substantially rectangular shaped base section having a longitudinal length which is greater than the height and thickness thereof and a height substantially greater than the thickness thereof; and
   a nose section extending integrally from the substantially rectangular shaped base section, the nose section tapering distally and inwardly from the base section.

15. An implant as recited in claim 14, wherein the base section has first and second sides, each side having a plurality of serrations therein.

16. An implant as recited in claim 14, further comprising a canal section along the longitudinal axis of the implant.

17. An implant as recited in claim 14, wherein the nose section is substantially shorter than the base section.

18. An implant as recited in claim 14, wherein the implant has a length in the range of about 20 mm to about 40 mm, a height in the range of about 8 mm to about 25 mm, and a thickness in the range of about 4 mm to about 12 mm.

19. A implant as recited in claim 14, wherein the implant has a height in the range of about 12 mm to about 20 mm and a thickness in the range of about 8 mm to about 12 mm.

20. A spinal vertebral implant configured to foster bone fusion between upper and lower adjacent spinal vertebrae between which the implant is placed pursuant to a spinal surgical procedure, the spinal vertebral implant comprising:
   substantially rectangular shaped base section having a longitudinal length which is greater than the thickness height thereof, the height being greater than the thickness, such that the implant can be conveniently placed between the vertebrae and maintain distraction of the anterior portions of the vertebrae; and
   a nose section extending integrally from the substantially rectangular shaped base section, the nose section comprising a solid piece of bone, the nose and base section comprising a longitudinal section of cortical bone having a grain oriented parallel to the longitudinal axis of the implant.

* * * * *

UNITED STATES PATENT AND TRADEMARK OFFICE
CERTIFICATE OF CORRECTION

PATENT NO. : 6,443,987 B1  Page 1 of 4
APPLICATION NO. : 09/662434
DATED : September 3, 2002
INVENTOR(S) : Donald W. Bryan It is certified that error appears in the above-identified patent and that said Letters Patent is hereby corrected as shown below:

Title Page
Item 56, U.S Patent Documents, change reference "4,742,256" to --4,743,256--

Title Page
Page 2, Column 2, Other Publications, Line 34, change "sistem" to --system--

Drawings
Replace FIG 8B to the figure depicted herein below, wherein the handle "62" has been changed to --67-- As shown in attached sheet

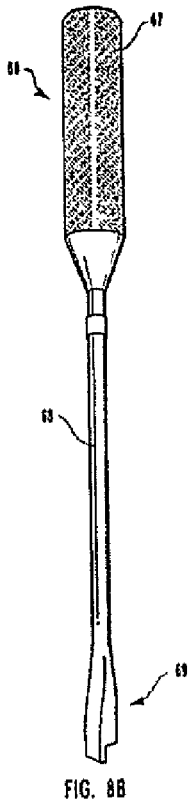

FIG. 8B

Column 1
Line 51, after "rather", change "then" to --than--

Column 6
Line 20, after "12", insert --mm--
Line 21, change "millimeters" to --mm--

UNITED STATES PATENT AND TRADEMARK OFFICE
CERTIFICATE OF CORRECTION

PATENT NO.        : 6,443,987 B1
APPLICATION NO. : 09/662434
DATED              : September 3, 2002
INVENTOR(S)     : Donald W. Bryan It is certified that error appears in the above-identified patent and that said Letters Patent is hereby corrected as shown below:

Column 8
Line 14, after "implant", remove "to"

Column 9
Line 15, change "slots" to --slot--

Column 10
Line 46, change "invertertebral" to --intervertebral--
Line 65, after "until", change "a" to --an--

Column 11
Line 27, after "space", change "if" to --is--

Column 12
Line 19, change "Nos." to --No.--
Line 43, change "vertebra" to --vertebrae--

Column 13
Line 22, after "handle", change "62" to --67--
Line 23, after "handle", change "62" to --67--
Line 25, after "member", change "62" to --60--
Line 28, change "position" to --positioned--
Line 31, after "member", change "62" to --60--
Line 45, change "comprise" to --comprises--

Column 15
Line 40, after "inserting", change "a" to --an--

Column 16
Line 42, change "comes" to --come--

UNITED STATES PATENT AND TRADEMARK OFFICE
CERTIFICATE OF CORRECTION

PATENT NO.        : 6,443,987 B1
APPLICATION NO. : 09/662434
DATED             : September 3, 2002
INVENTOR(S)       : Donald W. Bryan It is certified that error appears in the above-identified patent and that said Letters Patent is hereby corrected as shown below:

<u>Column 18</u>
Line 19, change "A" to --An--
Line 26, before "substantially", insert --a--
Line 27, after "thickness", insert --and--

Signed and Sealed this

Thirty-first Day of July, 2007

JON W. DUDAS
*Director of the United States Patent and Trademark Office*